US005739276A

United States Patent [19]
Shon et al.

[11] Patent Number: 5,739,276
[45] Date of Patent: Apr. 14, 1998

[54] CONOTOXIN PEPTIDES

[75] Inventors: Ki-Joon Shon, Shaker Heights, Ohio; Michelle M. Grilley; Baldomero M. Olivera, both of Salt Lake City, Utah

[73] Assignee: University of Utah Research Foundation, Salt Lake City, Utah

[21] Appl. No.: 624,123

[22] Filed: Mar. 29, 1996

Related U.S. Application Data

[63] Continuation-in-part of Ser. No. 423,561, Apr. 17, 1995, abandoned, which is a continuation-in-part of Ser. No. 319,554, Oct. 7, 1994.

[51] Int. Cl.[6] .................. A61K 38/17; C07K 14/435
[52] U.S. Cl. .................. 530/324; 514/12; 514/21
[58] Field of Search .................. 530/324; 514/12, 514/21

[56] References Cited

U.S. PATENT DOCUMENTS

| | | | |
|---|---|---|---|
| 4,447,356 | 5/1984 | Olivera et al. | 530/327 |
| 5,051,403 | 9/1991 | Miljanich et al. | 514/12 |
| 5,189,020 | 2/1993 | Miljanich et al. | 514/12 |
| 5,264,371 | 11/1993 | Miljanich et al. | 436/503 |
| 5,424,218 | 6/1995 | Miljanich et al. | 436/503 |
| 5,432,155 | 7/1995 | Olivera et al. | 517/12 |
| 5,514,774 | 5/1996 | Olivera et al. | 530/324 |

FOREIGN PATENT DOCUMENTS

| | | |
|---|---|---|
| WO 93/10145 | 5/1993 | WIPO . |
| WO 93/13128 | 7/1993 | WIPO . |
| WO 95/11256 | 4/1995 | WIPO . |

OTHER PUBLICATIONS

Shon et al. Purification, Characterization, Synthesis, and Cloning . . . Advance ACS Abstracts. Apr. 2, 1995.

Colledge, C.J. et al. (1992). "Precursor Structure of ω–Conotoxin GVIA Determined from a cDNA Clone," *Toxicon* 30:1111–1116.

Cruz, L.J. and Olivera, B.M. (1986). "Calcium Channel Antagonists. ω–Conotoxin Defines a New High Affinity Site," *J. Biol. Chem.* 261:6230–6233.

Dudley, S.C. et al. (1995). "A μ–Conotoxin–Insensitive $Na^+$Channel Mutant: Possible Localization of a Binding Site at the Outer Vestibule," *Biophysical J.* 69:1657–1665.

Fainzilber, M. et al. (1991). "Mollusc–specific toxins from the venom of *Conus textile neovicarius*," *Eur. J. Biochem.* 202:589–595.

Fainzilber, M. et al. (1994). "A New Neurotoxin Receptor Site on Sodium Channels Is Identified by a Conotoxin That Affects Sodium Channel Inactivation in Molluscs and Acts as an Antagonist in Rat Brain," *J. Biol. Chem.* 269:2574–2580.

Fainzilber, M. et al. (1994). "New Mollusc–Specific α–Conotoxins Block *Aplysia* Neuronal Acetylcholine Receptors," *Biochemistry* 33:9523–9529.

Gray, W.R. et al. (1981). "Peptide Toxins from *Conus geographus* Venom," *J. Biol. Chem.* 256:4734–4740.

Hasson, A. et al. (1993). "Alteration of Sodium Currents by New Peptide Toxins From the Venom of a Molluscivorous Conus Snail," *Eur. J. Neurosci.* 5:56–64.

(List continued on next page.)

*Primary Examiner*—Jeffrey E. Russel
*Attorney, Agent, or Firm*—Rothwell, Figg, Ernst & Kurz, P.C.

[57] ABSTRACT

The present invention is directed to δ-conotoxin PVIA having the formula Glu-Ala-Cys-Tyr-Ala-$Xaa_1$-Gly-Thr-Phe-Cys-Gly-Ile-Lys-$Xaa_2$-Gly-Leu-Cys-Cys-Ser-Glu-Phe-Cys-Leu-Pro-Gly-Val-Cys-Pro-Gly ($Xaa_1$ or $Xaa_2$ is Pro or 4-trans-hydroxyproline) (SEQ ID NO:7). The C-terminus may be free or amidated. This latter conotoxin is vertebrate-specific which targets voltage-sensitive Na channels.

9 Claims, 1 Drawing Sheet

OTHER PUBLICATIONS

Hillyard, D.R. et al. (1989). "A Molluscivorous Conus Toxin: Conserved Frameworks in Conotoxins," *Biochemistry* 28:358–361.

Hillyard, D.R. et al. (1992). "A New Conus Peptide Ligand for Mammalian Presynaptic $Ca^{2+}$ Channels," *Neuron* 9:69–77.

Hopkins, C. et al. (1995). "A New Family of Conus Peptides Targeted to the Nicotinic Acetylcholine Receptor," *J. Biol. Chem.* 270:22361–22367.

Kobayashi, J. et al. (1982). "Isolation of a Cardiotonic Glycoprotein, Striatoxin, from the Venom of the Marine Snail *Conus Striatus*," *Biochem. Biophys. Res. Comm.* 105:1389–1395.

Lundy, P.M. et al. (1991). "Pharmacological evidence for an $\omega$–conotoxin, dihydropyridine–insensitive neuronal $Ca^{2+}$ channel," *Eur. J. Pharmacol.* 206:61–68.

McCleskey, E.W. et al. (1987). "$\omega$–Conotoxin: Direct and persistent blockade of specific types of calcium channels in neurons but not muscle," *Proc. Natl. Acad. Sci. USA* 84:4327–4331.

McIntosh, M. et al. (1982). "Isolation and Structure of a Peptide Toxin from the Marine Snail *Conus magus*," *Arch. Biochem. Biophys.* 218:329–334.

McIntosh, J.M. et al. (1995). "A New Family of Conotoxins That Blocks Voltage-gated Sodium Channels," *J. Biol. Chem.* 270:16796–16802.

Monje, V.D. et al. (1993). "A New Conus Peptide Ligand For Ca Channel Subtypes," *Neuropharmacology* 32:1141–1149.

Myers, R.A. et al. (1993). "Conus Peptides as Chemical Probes for Receptors and Ion Channels," *Chem. Rev.* 93:1923–1936.

Olivera, B.M. et al. (1984). "Purification and Sequence of a Presynaptic Peptide Toxin from *Conus geographus* Venom," *Biochemistry* 23:5087–5090.

Olivera, B.M. et al. (1985). "Peptide Neurotoxins from Fish–Hunting Cone Snails," *Science* 230:1338–1343.

Olivera, B.M. et al. (1987). "Neuronal Calcium Channel Antagonists. Discrimination between Calcium Channel Subtypes Using $\omega$–Conotoxin from *Conus magus* Venom," *Biochemistry* 26:2086–2090.

Olivera, B.M. et al. (1990). "Diversity of Conus Neuropeptides," *Science* 249:257–263.

Olivera, B.M. et al. (1991). "Conotoxins," *J. Biol. Chem.* 266:22067–22070.

Ramilo, C.A. et al. (1992). "Novel $\alpha$–and $\omega$–Conotoxins from *Conus striatus* Venom," *Biochemistry* 31:9919–9926.

Regan, L.J. et al. (1991). "Ca2+ Channels in Rat Central and Peripheral Neurons: High–Threshold Current Resistant to Dihydropyridine Blockers and $\omega$–Conotoxin," *Neuron* 6:269–280.

Rivier, J. et al. (1987). "Neuronal Calcium Channel Inhibitors. Synthesis of $\omega$–Conotoxin GVIA and Effects on $^{45}Ca$ Uptake by Synaptosomes," *J. Biol. Chem.* 262:1194–1198.

Shon, K–J. et al. (1994). "$\delta$–Conotoxin GmVIA, a Novel Peptide from the Venom of *Conus gloriamaris*," *Biochemistry* 33:11420–11425.

Shon, K–J. et al. (1995). "Purification, Characterization, Synthesis, and Cloning of the Lockjaw Peptide from *Conus purpurascens* Venom," *Biochemistry* 34:4913–4918.

Spira, M.E. et al. (1993). "Chemical and Electrophysiological Characterization of New Peptide Neurotoxins form the Venom of the Molluscivorous Snail *Conus textile neovicarius*: A Review," *Isr. J. Med. Sci.* 29:530–543.

Woodward, S.R. et al. (1990). "Constant and hypervariable regions in conotoxin propeptides," *EMBO J.* 9:1015–1020.

Yoshikami, D. et al. (1989). "The Inhibitory Effects of Omega–Conotoxins on Ca Channels and Synapses," *Ann. N.Y. Acad. Sci.* 560:230–248.

Fainzilber, M. et al. (1995). "A New Conotoxin Affecting Sodium Current Inactivation Interacts with the $\delta$–Conotoxin Receptor Site," *J. Biol. Chem.* 270:1123–1129.

SIGNAL SEQUENCE 1. met lys leu thr cys val val ile val ala val leu leu leu thr ala
2. met lys leu thr cys met met ile val ala val leu phe leu thr ala
3. met lys leu thr cys val met ile val ala val leu phe leu thr ala
   ATG AAA CTG ACG TGC GTG ATG ATC GTT GCT GTG CTG TTC TTG ACT GCC cys gln leu ile thr ala asp asp ser arg --- gly thr gln lys his
trp thr phe ala thr ala asp asp pro arg asn gly leu gly asn leu
trp thr phe val thr ala asp asp ser lys asn gly leu glu asn his
TGG ACA TTC GTC ACG GCT GAT GAC TCC AAA AAT GGA CTG GAG AAT CAT --- --- arg ala leu gly ser thr thr --- --- glu leu ser --- leu
phe ser asn ala his his glu met lys asn pro glu ala ser lys leu
phe trp lys ala arg asp glu met lys asn arg glu ala ser lys leu
TTT TGG AAG GCA CGT GAC GAA ATG AAG AAC CGC GAA GCC TCT AAA TTG ser thr arg --- --- cys lys ser pro gly ser ser cys ser pro thr
asn lys arg --- trp cys lys gln ser gly glu met cys asn leu leu
asp lys lys glu ala cys tyr ala pro gly thr phe cys gly ile lys
GAC AAA AAG GAA GCC TGC TAT GCG CCT GGT ACT TTT TGT GGC ATA AAG

MATURE TOXIN ser tyr asn cys cys --- arg ser cys asn pro tyr thr lys arg cys
asp gln asn cys cys asp gly tyr cys ile val leu val --- --- cys
pro gly leu cys cys ser glu phe cys leu pro gly val --- --- cys
CCC GGG CTA TGC TGC AGT GAG TTT TGT CTC CCG GGC GTC --- --- TGC tyr gly        SEQ ID NO:12
thr            SEQ ID NO:13
phe gly gly    SEQ ID NO:10
TTC GGT GGT    SEQ ID NO:9

FIG. 1

CONOTOXIN PEPTIDES

CROSS-REFERENCE TO RELATED APPLICATION

The present application is a continuation-in-part of application Ser. No. 08/423,561 filed 17 Apr. 1995, now abandoned, which is a continuation-in-part of application Ser. No. 08/319,554 filed 7 Oct. 1994, which are incorporated herein by reference.

This invention was made with Government support under Grant No. POI GM 28677 awarded by the National Institutes of Health, Bethesda, Md. The United States Government has certain rights in the invention.

BACKGROUND OF THE INVENTION

This invention relates to relatively short peptides, and more particularly to peptides between about 25 and about 35 residues in length, which are naturally available in minute amounts in the venom of the cone snails or analogous to the naturally available peptides, and which include three cyclizing disulfide linkages.

The publications and other materials used herein to illuminate the background of the invention, and in particular, cases to provide additional details respecting the practice, are incorporated by reference, and for convenience are numerically referenced in the following text and respectively grouped in the appended bibliography.

Mollusks of the genus Conus produce a highly toxic venom which enables them to carry out their unique predatory lifestyle. Prey are immobilized by the venom which is injected by means of a highly specialized venom apparatus, a disposable hollow tooth which functions both in the mariner of a harpoon and a hypodermic needle.

Few interactions between organisms are more striking than those between a venomous animal and its envenomated victim. Venom may be used as a primary weapon to capture prey or as a defense mechanism. These venoms disrupt essential organ systems in the envenomated animal, and many of these venoms contain molecules directed to receptors and ion channels of neuromuscular systems.

The predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such, they are somewhat unusual. Peptides in this size range normally equilibrate among many conformations. Proteins having a fixed conformation are generally much larger.

The cone snails that produce these toxic peptides, which are generally referred to as conotoxins or conotoxin peptides, are a large genus of venomous gastropods comprising approximately 500 species. All cone snail species are predators that inject venom to capture prey, and the spectrum of animals that the genus as a whole can envenomate is broad. A wide variety of hunting strategies are used; however, every Conus species uses fundamentally the same basic pattern of envenomation.

The major paralytic peptides in these fish-hunting cone venoms were the first to be identified and characterized. In C. geographus venom, three classes of disulfide-rich peptides were found: the α-conotoxin peptides (which target and block the nicotinic acetylcholine receptors); the μ-conotoxin peptides (which target and block the skeletal $Na^+$ channels); and the ω-conotoxin peptides (which target and block the presynaptic neuronal $Ca^{2+}$ channels). However, there are multiple homologs in each toxin class; for example, there are at least five different ω-conotoxin peptides present in C. geographus venom alone. Considerable variation in sequence is evident, and when different ω-conotoxin peptide sequences were first compared, only the cysteine residues that are involved in disulfide bonding and one glycine residue were found to be invariant. Another class of conotoxins found in C. geographus venom is that referred to as conantokins, which cause sleep in young mice and hyperactivity in older mice and are targeted to the NMDA receptor. Each cone venom appears to have its own distinctive group, or signature, of different conotoxin sequences.

Many of these peptides have now become fairly standard research tools in neuroscience and can be used as chemical probes for receptors and ion channels (1). μ-Conotoxin peptides, because of their ability to preferentially block muscle but not axonal $Na^+$ channels, are convenient tools for immobilizing skeletal muscle without affecting axonal or synaptic events. ω-Conotoxin peptides have become standard pharmacological reagents for investigating voltage-sensitive $Ca^{2+}$ channels and are used to block presynaptic termini and neurotransmitter release. Several conotoxin peptides have also found utility in screening newly isolated conotoxin peptides or analogs for medical purposes (2).

SUMMARY OF THE INVENTION

The present invention is directed to conotoxin peptides having 25–35 amino acids, six cysteines which form three disulfide bonds between the first and fourth, second and fifth, and third and sixth cysteines, respectively. The invention is directed to δ-conotoxin GmVIA having the formula Val-Lys-Pro-Cys-Arg-Lys-Glu-Gly-Gln-Leu-Cys-Asp-Pro-Ile-Phe-Gln-Asn-Cys-Cys-Arg-Gly-Trp-Asn-Cys-Val-Leu-Phe-Cys-Val (SEQ ID NO:1). This peptide activates sodium channels. The invention is further directed to μO-conotoxin peptides of the generic formula Ala-Cys-Xaa$_1$-Lys-Lys-Trp-Glu-Tyr-Cys-Ile-Val-Pro-Ile-Xaa$_2$-Gly-Phe-Xaa$_3$-Tyr-Cys-Cys-Pro-Gly-Leu-Ile-Cys-Gly-Pro-Phe-Val-Cys-Val, wherein Xaa$_1$ is Arg or Ser, Xaa$_2$ is Ile or Leu and Xaa$_3$ is Ile or Val (SEQ ID NO:2). These μO-conotoxin peptides block sodium channels. Examples of μO-conotoxin peptides of the present invention are MrVIA, having the formula Ala-Cys-Arg-Lys-Lys-Trp-Glu-Tyr-Cys-Ile-Val-Pro-Ile-Ile-Gly-Phe-Ile-Tyr-Cys-Cys-Pro-Gly-Leu-Ile-Cys-Gly-Pro-Phe-Val-Cys-Val (SEQ ID NO:3), and MrVIB, having the formula Ala-Cys-Ser-Lys-Lys-Trp-Glu-Tyr-Cys-Ile-Val-Pro-Ile-Leu-Gly-Phe-Val-Tyr-Cys-Cys-Pro-Gly-Leu-Ile-Cys-Gly-Pro-Phe-Val-Cys-Val (SEQ ID NO:4). The invention is further directed to δ-conotoxin PVIA having the formula Glu-Ala-Cys-Tyr-Ala-Xaa$_1$-Gly-Thr-Phe-Cys-Gly-Ile-Lys-Xaa$_2$-Gly-Leu-Cys-Cys-Ser-Glu-Phe-Cys-Leu-Pro-Gly-Val-Cys-Pro-Gly (Xaa$_1$ or Xaa$_2$ is Pro or 4-trans-hydroxyproline) (SEQ ID NO:7). The C-terminus may be free or amidated. This latter conotoxin is vertebrate-specific which targets voltage-sensitive Na channels.

BRIEF DESCRIPTION OF THE FIGURE

FIG. 1 shows the nucleic acid sequence and predicted amino acid sequence of a cDNA clone encoding the lockjaw peptide precursor and a comparison of the lockjaw peptide to two other related Conus peptide precursor sequences.

DETAILED DESCRIPTION OF THE PREFERRED EMBODIMENT

The present invention is directed to conotoxin peptides having 25–35 amino acids, six cysteines which form three disulfide bonds between the first and fourth, second and fifth, and third and sixth cysteines, respectively. The invention is directed to δ-conotoxin GmVIA having the formula Val-Lys-Pro-Cys-Arg-Lys-Glu-Gly-Gln-Leu-Cys-Asp-Pro-Ile-Phe-Gln-Asn-Cys-Cys-Arg-Gly-Trp-Asn-Cys-Val-Leu-Phe-Cys-Val (SEQ ID NO:1). This peptide activates sodium channels and is useful as pesticides, e.g. against garden snails and slugs, using conventional techniques, including sprinkling, spraying or creating transgenic plants. The invention is further directed to μO-conotoxin peptides of the generic formula Ala-Cys-Xaa$_1$-Lys-Lys-Trp-Glu-Tyr-Cys-Ile-Val-Pro-Ile-Xaa$_2$-Gly-Phe-Xaa$_3$-Tyr-Cys-Cys-Pro-Gly-Leu-Ile-Cys-Gly-Pro-Phe-Val-Cys-Val, wherein Xaa$_1$ is Arg or Ser, Xaa$_2$ is Ile or Leu and Xaa$_3$ is Ile or Val (SEQ ID NO:2). These μO-conotoxin peptides block sodium channels and are useful as active agents for anti-seizures as am other sodium channel blockers. Examples of μO-conotoxin peptides of the present invention are MrVIA, having the formula Ala-Cys-Arg-Lys-Lys-Trp-Glu-Tyr-Cys-Ile-Val-Pro-Ile-Ile-Gly-Phe-Ile-Tyr-Cys-Cys-Pro-Gly-Leu-Ile-Cys-Gly-Pro-Phe-Val-Cys-Val (SEQ ID NO:3), and MrVIB, having the formula Ala-Cys-Ser-Lys-Lys-Trp-Glu-Tyr-Cys-Ile-Val-Pro-Ile-Leu-Gly-Phe-Val-Tyr-Cys-Cys-Pro-Gly-Leu-Ile-Cys-Gly-Pro-Phe-Val-Cys-Val (SEQ ID NO:4). The invention is further directed to δ-conotoxin PVIA having the formula Glu-Ala-Cys-Tyr-Ala-Xaa$_1$-Gly-Thr-Phe-Cys-Gly-Ile-Lys-Xaa$_2$-Gly-Leu-Cys-Cys-Ser-Glu-Phe-Cys-Leu-Pro-Gly-Val-Cys-Pro-Gly (Xaa$_1$ or Xaa$_2$ is Pro or 4-trans-hydroxyproline) (SEQ ID NO:7). The C-terminus may be free or amidated. This latter conotoxin is vertebrate-specific which targets voltage-sensitive Na channels and is useful as an active agent for muscle contraction in instances where lack of muscle contraction is problematic, such as for treating urinary or fecal incontinence. Each of these conotoxins is also useful for tagging tumors since they are able, as are other conotoxins, to detect antibodies which form against tumors. Since conotoxins bind to cell surface receptors, ion channels, they are capable of inhibiting tumor growth and are useful as anti-neoplastic agents.

Despite the close relationship of the δ-conotoxins to the ω-conotoxins, it is clear that they have different physiological targets. The ω-conotoxins inhibit voltage-gated $Ca^{2+}$ channels, distinguishing various subtypes. In contrast, the δ-conotoxins are without effect on $Ca^{2+}$ channels; the results shown below demonstrate they do not compete for binding with ω-conotoxin GVIA and do not induce the shaking syndrome in mice characteristic of the ω-conotoxins.

The electrophysiological results presented below demonstrate that δ-conotoxin GmVIA prolongs spike duration by slowing the inactivation kinetics of the sodium current, and thus at the gross physiological level it appears to have effects similar to those of δ-conotoxin TxVIA (3). Detailed electrophysiological studies described herein provide evidence that δ-conotoxin GmVIA specifically targets $Na^+$ channels and prolongs the action potential duration by slowing down the sodium current inactivation. The data clearly indicate that there are significant differences between GmVIA and TxVIA at a detailed mechanistic level. In many ways, this is not surprising because of the tremendous sequence divergence between GmVIA and TxVIA.

Biologically active δconotoxin GmVIA has been chemically synthesized, demonstrating that the biological activity is not due to contaminants. A different family of Conus peptides, the μ-conotoxins, is known which also affects $Na^+$ channels. However, these have a different disulfide framework, are channel blockers specific for the muscle subtype, and, like the ω-conotoxins, are highly basic molecules. Given the very different chemical character of δ-conotoxins, it is likely that their site of action on the $Na^+$ channel is quite distinct.

δ-Conotoxin GmVIA, the major component present in the venom of the mollusc hunting snail *C. gloriamaris*, elicits spike broadening at a concentration of 0.5 μM. Voltage clamp analysis reveals that the effects of the toxin are expressed by: Slowing down the rate of the early sodium current inactivation; induction of a late slowly inactivating sodium current which is not detectable in control experiments; Shifting the steady state sodium current inactivation curve to more depolarized values and shifting the activation curve to more hyperpolarized values. These changes are not associated with an increase in the rate of rise of the early sodium current or by a change in the peak sodium current.

Sodium current inactivation experiments show that the toxin modifies the sodium current inactivation kinetics from a single exponential with an average τ=0.47±0.14 ms to a slower decay which can be described by two time constants: the initial inactivation phase has a τ=0.86±0.12 ms, and the second phase a τ=488±120 ms. These changes in time constants may account for the typical alterations in the action potential shape induced by δ-conotoxin GmVIA. In artificial sea water (ASW) and in the presence of the toxin, the early fast phase of the action potential and its plateau corresponds to the early rapidly inactivating sodium current and the long-lasting, slowly inactivating phase.

The amplitude of the late phase of the sodium current induced by δ-conotoxin GmVIA is independent of the amplitude of the early current. Thus, even when the early current is completely inactivated by a prepulse, the amplitude of the late component is not reduced. The simplest explanation to account for this observation is that the toxin alters the inactivation kinetics of the entire population of sodium channels from a single time constant to dual time constants. If this assumption is right, then the observations suggest that in the presence of δ-conotoxin-GmVIA, the sodium channels can be inactivated in two modes: In the one mode they go through the rapid inactivation phase to the slow inactivating phase, or alternatively are "switched" directly into the slowly inactivating mode without going first through the rapidly inactivating phase. An alternative explanation assumes that the toxin activates a population of silent, slowly inactivating sodium channels. This hypothesis is also consistent with the finding that the non-inactivating phase can be activated independently of the early sodium content. However, since the peak of the early sodium current is not increased in the presence of the toxin as would be expected if additional sodium channels were activated, then this hypothesis seems to be less likely.

The macroscopic effects of the toxin purified from the venom of the shallow water mollusc hunting snail *C. textile* (3) and the one purified from the deep water *C. gloriamaris* are similar but not identical. Both toxins alter the inactivation kinetics of the sodium current from a process that is best described by a single exponent into a biphasic process. However, the effects of the two toxins differ because δ-conotoxin GmVIA induces a significantly longer, slow inactivation phase than that induced by δ-conotoxin TxVIA. Additionally, the effects of δ-conotoxin TxVIA undergo desensitization in the presence of the toxin, whereas the effects of δ-conotoxin GmVIA are observed for as long as the toxin is present in the bathing solution. It is reasonable to assume that these peptide toxins target the same ligand binding pocket of the sodium channel: Both peptides are extremely hydrophobic, a characteristic which may be important for binding to this specific site. Nevertheless, the differences in the primary sequences of these peptides cause a clear difference in their detailed effects on sodium current inactivation kinetics.

Biologically active δ-conotoxin PVIA has been chemically synthesized, demonstrating that the biological activity is not due to contaminants. δ-Conotoxin PVIA (sometimes called herein the lockjaw peptide), present in the venom of the fish hunting snail *C. purpurascens*, is the first biochemically characterized toxin shown to underlie such symptoms, as well as to increase excitability at the vertebrate neuromuscular junction. When the peptide was injected into fish intraperitoneally or intramuscularly, a characteristic rapid and very jerky swimming behavior was followed by rigid paralysis, the lockjaw syndrome, and death. Excitotoxin activities were also induced upon intracranial injection of the peptide into mice.

The data presented below strongly indicate that the lockjaw peptide is a vertebrate-targeted δ-conotoxin. The *C. purpurascens* lockjaw peptide was inactive in the molluscan test system at doses 100-fold higher than required to potently affect both fish and mice. In contrast, δ-conotoxin TxVIA which potently potentiates molluscan Na channels showed no biological activity in any assays involving vertebrate systems.

Nevertheless, δ-conotoxin TxVIA and the lockjaw peptide competed for the same binding site in rat brain membranes. δ-Conotoxin TxVIA binds specifically and with high affinity to voltage-sensitive sodium channels in the mammalian central nervous system, even though it has no inhibitory effect (29). Taken together, the primary structure of the lockjaw peptide, the predicted amino acid sequence of the precursor, the electrophysiological results using the frog neuromuscular junction, the binding data, and the in vivo symptoms induced by the peptide are consistent with the conclusion that the lockjaw peptide is a vertebrate-targeted δ-conotoxin. In contrast to previously characterized δ-conotoxins (TxVIA and GmVIA) which had no effects on cloned rat brain Na channels, δ-conotoxin PVIA had clear effects on this mammalian channel. Under depolarizing conditions, the toxin inhibited channel inactivation. A persistent conductance was observed in the presence of this peptide. That is, when voltage is brought from a resting potential to 0 mV and held there for 18 mseconds, virtually no conductance remains in the control, whereas a residual Na conductance remains in the presence of δ-conotoxin PVIA.

The cloning data described below demonstrate that the toxin precursor must have an amidated C-terminus. The amidated lockjaw peptide is designated as δ-conotoxin PVIA and the form of the peptide with the free carboxyl terminus as [deamido]-δ-conotoxin PVIA. It should be noted that another fish-hunting Conus species, *Conus striatus*, has a toxin which apparently acts by the same physiological mechanism. However, the purified toxin from *C. striatus* (striatotoxin) has been reported to have a much higher molecular mass ($\approx$25 kDa) (48) which would appear to make it distinct from all of the δ-conotoxins characterized so far.

In a survey of a dozen Conus venoms, a broad spectrum of mammalian excitotoxins was found to be present. Previously characterized conotoxins (α-, μ- and ω-) all cause a decrease in electrical excitability or an inhibition of neurotransmission (1, 43). The comprehensive biochemical characterization and successful chemical synthesis of δ-conotoxin PVIA is the first description of a vertebrate-targeted excitotoxin from Conus venoms.

Despite the close relationship of the precursor sequences of the μO-conotoxins to ω-conotoxin GVIA and to δ-conotoxin TxVIA, it is clear that they have different physiological targets. The ω-conotoxins inhibit voltage-gated $Ca^{2+}$ channels, distinguishing various subtypes. The δ-conotoxins activate $Na^+$ channels. In contrast, the μO-conotoxins are without effect on $Ca^{2+}$ channels; the results show that they do not compete for binding with ω-conotoxin GVIA and do not induce the shaking syndrome in mice characteristic of the ω-conotoxins. Instead of activating the $Na^+$ channels, the μO-conotoxins block these channels.

The electrophysiological results presented below demonstrate that μO-conotoxin MrVIA specifically targets $Na^+$ channels and blocks the action potential and inward sodium current. The block is not associated with a change in the current voltage relationships. Biologically active μO-conotoxins have been chemically synthesized, demonstrating that the activity is not due to contaminants.

Voltage clamp analysis reveals that ten seconds after toxin application to reach a final bath concentration of 350 nM, the sodium action potential was blocked. An increase in the stimulus intensity after the blockade of the action potential failed to elicit a regenerative response. To directly examine the toxin action on sodium, calcium and potassium currents, the whole-cell patch clamp configuration was used. The inward $I_{Na+}$ evoked by depolarizing the neuron from a holding potential of −50 to 20 mV was completely blocked 30 seconds following the application of 250 nM MrVIA. Partial blockage of $I_{Na+}$ by 40 nM toxin revealed that the block is not associated with a change in the current voltage relationships. Patch clamp experiments revealed that calcium and potassium currents are not affected by the toxin.

Binding competition experiments demonstrate that competitive binding inhibition by μO-conotoxin MrVIA does not occur for the high affinity ω-conotoxin GVIA binding site on mammalian brain $Ca^{2+}$ channels. Electrophysiological experiments show that μO-conotoxin MrVIA and δ-conotoxin TxVIA elicit opposite effects, since δ-conotoxin TxVIA is an excitotoxin which increases $Na^+$ conductance (3). Thus, although μO-, ω- and δ-conotoxins apparently belong to the same protein superfamily, they have strikingly different physiological effects. In contrast, the functionally homologous μ-conotoxin GIIIA has an unrelated disulfide structure, and its precursor sequence shows no homology whatsoever to the μO-conotoxins from *C. marmoreus*. Thus, the peptides provide molecular guideposts for species diversification in this genus. The genetic analysis shows that the μO-conotoxins, Na channel inhibitors from *C. marmoreus*, were independently evolved from the μ-conotoxins from fish-hunting Conus. Thus, in this single genus, one protein superfamily comprises multiple functionally-distinct toxin classes, but functional convergence of two sodium channel-blocking toxins from different superfamilies is also observed.

These peptides, which are generally termed δ- or μO-conotoxin peptides, are sufficiently small to be chemically synthesized. General chemical syntheses for preparing the foregoing conotoxin peptides are described hereinafter, along with specific chemical syntheses of several conotoxin peptides and indications of biological activities of these synthetic products. Various ones of these conotoxin peptides can also be obtained by isolation and purification from specific Conus species using the technique described in U.S. Pat. No. 4,447,356 (4), the disclosure of which is incorporated herein by reference.

Although the conotoxin peptides of the present invention can be obtained by purification from the enumerated cone snails, because the amounts of conotoxin peptides obtainable from individual snails are very small, the desired substantially pure conotoxin peptides are best practically obtained in commercially valuable amounts by chemical synthesis. For example, the yield from a single cone snail may be about 10 micrograms or less of conotoxin peptide. By "substantially pure" is meant that the peptide is present in the substantial absence of other biological molecules of the stone type; it is preferably present in an amount of at least about 85% by weight and preferably at least about 95% of such biological molecules of the same type which are present (i.e., water, buffers mad innocuous small molecules may be present). Chemical synthesis of biologically active conotoxin peptides depends of course upon correct determination of the amino acid sequence.

The conotoxin peptides can also be produced by recombinant DNA techniques well known in the art. Such techniques are described by Sambrook et al. (5) The peptides produced in this manner are isolated, reduced if necessary, and oxidized to form the correct disulfide bonds.

One method of forming disulfide bonds in the conotoxin peptides of the present invention is the air oxidation of the linear peptides for prolonged periods under cold room temperatures. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration because the cross-linking and/or rearrangement which occurs in vivo has been found to create the biologically potent conotoxin molecule. However, because of the dilution resulting from the presence of other fractions of less biopotency, a somewhat higher dosage may be required.

A second method of forming the disulfide bonds in the conotoxin peptides of the present invention involves the use of acetamidomethyl (Acm) as protection agent on the second and fifth cysteines during the synthesis of the conotoxin peptides. The use of Acm on these two residues is based on the analogy with disulfide bridges in other conotoxin peptides. The peptide with the Acm protected cysteines is air-oxidized overnight at room temperature. The bicyclic peptides are separated by high performance liquid chromatography (HPLC) and the desired isomer isolated. The final disulfide bridge is carried out by iodination. The undesired isomers are efficiently recycled by reduction to linear peptide. The desired isomer is determined by a partial reduction analysis (6). In this analysis, a sample of a bicyclic precursor is treated with tris-[2-carboxyethyl]-phosphine to give linear peptide and a singly-bridged intermediate. The latter peptide is reacted with iodoacetamide, and the location of alkylated cysteine residues is established by sequence analysis. In this analysis, it was determined that the correct linkages were between the first and fourth, second and fifth, and third and sixth cysteines for GmVIA, for example.

The peptides are synthesized by a suitable method, such as by exclusively solid-phase techniques, by partial solid-phase techniques, by fragment condensation or by classical solution couplings. The employment of recently developed recombinant DNA techniques may be used to prepare these peptides, particularly the longer ones containing only natural amino acid residues which do not require post-translational processing steps.

In conventional solution phase peptide synthesis, the peptide chain can be prepared by a series of coupling reactions in which the constituent amino acids are added to the growing peptide chain in the desired sequence. The use of various N-protecting groups, e.g., dicyclohexylcarbodiimide or carbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (7). Techniques of exclusively solid-phase synthesis are set forth in the textbook, "Solid-Phase Peptide Synthesis," (8), and are exemplified by the disclosure of U.S. Pat. No. 4,105,603 (9). The fragment condensation method of synthesis is exemplified in U.S. Pat. No. 3,972,859 (10). Other available syntheses are exemplified by U.S. Pat. Nos. 3,842,067 (11) and 3,862,925 (12).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et al. (13). Chloromethylated resins are commercially available from Bio Rad Laboratories (Richmond, Calif.) and from Lab. Systems, Inc. The preparation of such a resin is described by Stewart et al. (8). BHA and MBHA resin supports are commercially available, and are generally used when the desired polypeptide being synthesized has an unsubstituted amide at the C-terminus. Thus, solid resin supports may be any of those known in the art, such as one having the formulae —O—CH$_2$-resin support, —NH BHA resin support, or —NH— MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (14) can be used, or should still other groups than the free acid be desired at the C-terminus, it may be preferable to synthesize the peptide using classical methods as set forth in the Houben-Weyl text (7).

The C-terminal amino acid, protected by Boc and by a side-chain protecting group, if appropriate, can be first coupled to a chloromethylated resin according to the procedure set forth in K. Horiki et al. (15), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (16).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (16) and Kapoor (17).

Each protected amino acid or amino acid sequence is introduced into the solid-phase reactor in about a twofold or more excess, and the coupling may be carried out in a medium of dimethylformamide (DMF): CH$_2$Cl$_2$ (1:1) or in DMF or CH$_2$Cl$_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (18). Coupling reactions can be performed automatically, as on a Beckman 990 automatic synthesizer, using a program such as that reported in Rivier et al. (19).

After the desired amino acid sequence has been completed, the intermediate peptide can be removed from the resin support by treatment with a reagent, such as liquid hydrogen fluoride, which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptidoresin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF), followed by oxidation as described above.

EXAMPLES

The present invention is described by reference to the following Examples, which are offered by way of illustration and are not intended to limit the invention in any manner. Standard techniques well known in the art or the techniques specifically described below were utilized.

Example 1

Identification of δ-Conotoxin Peptide GmVIA Sequence

Specimens of *C. gloriamaris* were dissected, and the venom ducts were removed. The venom was squeezed and scraped from the ducts as described by Cruz et al. (20) and then lyophilized. Tris-(2-carboxyethyl)phosphine (TCEP) was synthesized by the method of Burns et al. (21).

Lyophilized venom (200 mg) was first suspended in 5 mL of 0.1% TFA and 40% acetonitrile and soaked for 10 minutes over ice with occasional stirring and sonication. The solution was then centrifuged for 5 minutes using a bench-top microfuge and the supernatant was saved. The extraction procedure was repeated two more times with the same solvent and twice with 5 mL of 0.1% TFA and 90% acetonitrile. Supernatants from all extractions were combined and stored over ice while awaiting further purification. The pellet was dried and weighed.

Pooled venom extracts were subjected to reversed-phase high pressure liquid chromatography (HPLC) using a C$_8$ Aquapore semipreparative column (7.0×250 mm; 4 mL/min). Secondary purification was carried out on a C$_{18}$ Vydac column (218TP54, 4.6×250 mm; 1 mL/min). HPLC buffers were (A) 0.1% TFA in water, and (B) 0.09% TFA in 90% acetonitrile. For both semipreparative and analytical runs, peptides were eluted with a linear gradient of 1% buffer B increase/min. The C$_{18}$ Vydac analytical column was also used for purifying partially reduced intermediates and alkylated peptides during disulfide bridge analysis.

Disulfides were reduced by incubating equal volumes of peptide solution and 8 mM TCEP in 0.25M Tris, pH 8.0, for 20 minutes at room temperature. A single product was obtained by reversed-phase HPLC on the $C_{18}$ Vydac analytical column. The reduced peptide was alkylated by the addition of 1 μL of 4-VP/100 μL of peptide solution. After incubation for 20–30 minutes in the dark, the solution was diluted to reduce acetonitrile concentration, and the pyridylethylated peptide was repurified by reversed-phase HPLC. The eluted peptide was adsorbed onto Biobrene-treated glass fiber filters, and the amino acid sequence was analyzed by automated Edman degradation on an ABI Model 477A instrument.

Analysis of pyridylethylated peptide by standard Edman chemistry gave the sequence shown in SEQ ID NO:1. Completeness of the sequence was indicated by mass analysis using LSIMS. The observed $(M+H)^+$ was consistent with the above sequence, having a free carboxyl at the C-terminus and three disulfide bridges (monoisotopic; observed $(M+H)^+$=3352.5; theory, 3352.51). Thus, the peptide has 29 amino acids, and its six cysteine residues are arrayed in the pattern (—C—C—CC—C—C—) typical of the ω-conotoxins and δ-conotoxin TxVIA. Both δ-conotoxins lack the C-terminal amidation characteristic of most conotoxins.

Disulfide bridge analysis was carried out by the partial reduction method of Gray (6). δ-Conotoxin GmVIA in HPLC column effluent was added to an equal volume of 20 nM TCEP in 0.17M sodium citrate, pH 3.0, and incubated for 5 minutes at 64° C. The partially reduced species were purified by HPLC and were immediately frozen in solution (pH 2.0) at –40° C. to prevent disulfide exchange. For convenience, and to minimize loss of peptide, all intermediates were kept in the HPLC effluent without drying them down completely. Partially reduced peptide were alkylated by squirting 100 μL of thawed peptide solution into a supersaturated solution of IAM (100 mg in 200 μL of 0.5M Tris-acetate, pH 8.0, containing 2 mM EDTA), while the latter was mixed rapidly. After 20–30 seconds, the reaction was quenched by adding 450 μL of 0.5M citric acid solution. Alkylated peptides were purified by HPLC (analytical $C_{18}$ Vydac column with flow rate of 1 mL/min and an acetonitrile gradient increase 1%/min) and were then subjected to complete reduction and further alkylation by 4-VP as described previously.

The unusually high abundance of peptide in venom allowed the analysis of its disulfide bridge connectivity, using partial reduction by TCAP at pH 3.0 (6). No reduction was observed at room temperature, but a useful spectrum of products was obtained after five minutes at 64° C. Completely reduced (R) and native (N) peptides, and four partially reduced intermediates (PR1–PR4) were seen. Peptides PR1, -2 and -3 were further purified and analyzed. Reaction with iodoacetamide, using the rapid alkylation protocol proceeded with minimal rearrangement of the disulfides. All remaining Cys residues were pyridylethylated following full reduction and alkylation with 4-VP. Thus, every cysteine residue was converted either to Cys(CAM), if it had been part of a bridge which was reduced, or to Cys(PE), if it had been part of a bridge which had initially remained intact. The intermediates were then sequenced to locate the two labels.

Analysis of PR2 revealed labeling of Cys4 and Cys19 with CAM, and of the remaining cysteines with PE. This indicates that a bridge linking Cys4 and Cys19 was the only one which had been reduced. PR1 and PR3 proved to be monocyclic peptides in which only Cys11–Cys24 and Cys18–Cys28 remained intact, respectively. These results form a completely consistent set, indicating that the bridges are linked sequentially (4–19, 11–24 and 18–28) in the same pattern as that observed with the ω-conotoxins.

For comparison, the disulfide bridge connectivities of the related peptide δ-conotoxin TxVIA (27, 28) were also analyzed by the same methods. A generally similar pattern was obtained after partial reduction and analysis of intermediates 2 and 3 was sufficient to establish that the disulfide connectivity was the same as that of δ-conotoxin GmVIA.

Example 2

Synthesis of δ-Conotoxin Peptide GmVIA Sequence

δ-Conotoxin GmVIA was synthesized by the two-stage strategy employed for ω-conotoxin MVIID (22). The protected peptide resin was built using standard fmoc chemistry, couplings being carried out with equimolar amounts of amino acid derivative, DCC, HOBT. All amino acids were purchased from Bachem (Torrance, Calif.), and side chains were protected as follows: Arg (pmc), Asn (trt), Asp (t-bu), Gln (trt), Glu (t-bu), and Lys (boc). Cys residues 4, 18, 19 and 28 were protected by trt, while Cys residues 11 and 24 were protected by acm.

At the completion of synthesis, the terminal fmoc group was removed by standard treatment with piperidine/NMP (20% by volume). Peptide was removed from the resin by treatment for 2 hours at 20° C. with TFA/$H_2O$/ethanedithiol/phenol/thioanisole (90/5/2.5/7.5/5 by volume), and the whole mixture was filtered rapidly into t-butyl methyl ether at −10° C. Linear peptide, retaining protection only on Cys11 and Cys24, was collected as a pellet after centrifugation and was washed once with t-butyl methyl ether. The pellet dissolved readily in 60% acetonitrile containing 0.1% TFA; an ether layer that separated was discarded. Peptide solution was diluted with 0.1% aqueous TFA before application to a 2.5-×25-cm column of Vydac $C_{18}$. Elution was carried out at 20 mL/min, using a gradient of acetonitrile (27–45%) in 0.1% TFA. The major peptide-containing fraction was diluted with 30% acetonitrile, the pH was adjusted to 7.0 with NaOH, and the solution was stirred overnight at room temperature. This procedure oxidized Cys residues 4, 18, 19 and 28, generating three bicyclic isomers which were isolated by HPLC. In small-scale trials, one of these gave native-like material after oxidation with 2 mM $I_2$ in 10% TFA (10 min, 20° C., followed by a quench with 30 mM ascorbic acid). Oxidation was then carried out preparatively on that isomer, and the tricyclic peptide was isolated by HPLC.

Construction of the protected peptide resin proceeded smoothly. A single major product was obtained after deprotection and cleavage, accounting for 53% of the total absorbance at 220 nm. Air oxidation of this material gave the expected three bicyclic peptides, with a pattern similar to that obtained for ω-conotoxin MVIID (22). Treatment of the second of these bicyclic peptides resulted in approximately 60% conversion to a product having the same elution time as natural peptide. Coinjection experiments verified that the two products were indistinguishable by this method. Bioassays in the snail showed that synthetic peptide was equipotent with the natural.

Example 3

Identification of μO-Conotoxin Peptides MrVIA and MrVIB

Lyophilized crude venom (500 mg) was extracted (23), placed in a Centricon 30 microconcentrator, and centrifuged at 1500×g, for 8 hours at 4° C. Filtrate was purified on a $C_{18}$ Vydac column (22×250 mm) using a gradient system. Buffer A=0.1% trifluoroacetic acid (TFA) and buffer B=0.1% TFA, 60% acetonitrile. The gradient began at 0% B, increased to 15% B over 15 minutes, increased to 39% B over 72 minutes, increased to 65% B over 15 minutes, increased to 100% B over five minutes, and held at 100% B for 10 minutes. Flow rate was 10 ml/min. The very hydrophobic MrVIA and MrVIB elute as the last two major peaks at 109.4 and 110.3 minutes. The fraction eluting at 109.4 minutes was subjected to a second RPLC using a Vydac $C_8$ column (10×250 mm) with buffer A as above and buffer B=0.1% TFA, 90% acetonitrile. The gradient began at 5% B, increased to 55% B over 15 minutes, and increased to 70% B over 45 minutes. Flow rate was 5 ml/min. An analogous RPLC was performed to isolate MrVIB. Mass spectra were measured with a JEOL JMS-HX110 double-focusing spectrometer fitted with a $Cs^+$ gun. Sequencing was performed as previously described (24).

Liquid secondary ion mass spectrometry indicated that Cys residues are present as disulfides and that the C-terminal α-carboxyl group is the free acid for both peptides (monoisotopic $MH^+$: MrVIA calculated 3487.66, found 3487.8; MrVIB calculated 3404.58, found 3404.8). Biologically active μO-conotoxin MrVIA was synthesized in accordance with the techniques previously described.

Example 4

Identification of DNA for μO-Conotoxin Peptide MrVIB cDNA clones encoding the μO-conotoxin peptide MrVIB were isolated from a size-fractionated cDNA library constructed from C. magus venom duct mRNA. The cDNA library was size-fractionated into insets with average size of 74 Kb, 2 Kb, 1 Kb and 0.5 Kb. The two smallest size fractions were screened.

Five μg of DNA were denatured in 0.4M NaOH at 37° C. for 30 min. The solution was then neutralized by adding ammonium acetate to a final concentration of 0.4M, and the DNA precipitated with two volumes of absolute ethanol. The DNA was pelleted, resuspended in 8 μl of $H_2O$, and annealed with 2 pmols of primer by heating to 65° C. for 5 min and cooling slowly to 30° C. The DNA was sequenced using the Sequenase Version 2.0 DNA sequencing kit. Labeling and termination reactions were carried out according to protocol in the Sequenase Version 2.0 4th Edition Manual (United States Biochemical, 1990). Three cDNA clones for μO-conotoxin MrVIB were identified. The nucleic acid sequence and presumptive translation product for the encoded precursor are shown as SEQ ID NO:5 and SEQ ID NO:6, respectively.

Example 5

Identification of δ-Conotoxin Peptide PVIA Sequence

Milked Venom Extraction. C. purpurascens specimens were collected from the Gulf of California, and venom was collected by a milking procedure. Milked venom (0.5 ml) was pooled from 50 Eppendorf tubes stored in a −70° C. deep freezer. The pooled venom was kept over ice and diluted with 10 mL of 0.1% TFA in water. The solution was spun for a few minutes using a bench-top microfuge, and the supernatant was immediately subjected to purification. There were several prominent components of the venom; when these were tested for biological activity, several of the major peaks caused flaccid paralysis in fish. Some of these components have been shown to inhibit the nicotinic acetylcholine receptor. In a pooled venom preparation, the late-eluting fractions caused paralysis and death in fish accompanied by muscle contracture and the lockjaw symptoms (rapid running, seizures and convulsions) consistent with the increased excitability in the mammalian central nervous system.

Peptide Purification by HPLC. A preparative scale reversed-phase HPLC was used for first-line purification of the milked venom. The entire 10 mL was applied to a $C_{18}$ Vydac preparative column (22.0×250 mm; 20 mL/min) with a guard column (22.0×50.0 mm). As a secondary purification, a $C_{18}$ Vydac analytical column (218TP54, 4.6× 250 mm; 1 mL/min) was used. HPLC buffers were (A) 0.1% TFA in water and (B) 0.085% TFA in 90% acetonitrile. For both preparative and analytical runs, the peptides were eluted with a linear gradient of 1% buffer B increase per minute. The $C_{18}$ analytical column was also used for purifying alkylated peptides for amino acid sequence analysis. The major components which elicit these symptoms were purified to apparent homogeneity.

Amino Acid Sequence Analysis. Peptide reduction and alkylation protocols were as described in Shon et al. (38). Reversed-phase HPLC was used for repurifying alkylated peptide. The eluted peptide was adsorbed onto Biobrene-treated glass fiber filters, and the amino acid sequence was analyzed by automated Edman degradation on an ABI Model 477A instrument. The amino acid sequence of each homogeneous peptide was determined by standard Edman degradation procedures. The amino acid sequence of each homogeneous peptide was determined by standard Edman degradation procedures. The two sequencing runs gave the identical sequence, revealing a hydrophobic 29 amino acid, which is referred to as the lockjaw peptide. The purified components were analyzed by mass spectrometry, for one component, a mass (monoisotopic MH+=2997.2; theoretical 2997.22) consistent with the predicted sequence from the Edman degradation with an amidated C-terminus. Together, the sequencing data and the mass spectroscopy predict the sequence Glu-Ala-Cys-Tyr-Ala-$Xaa_1$-Gly-Thr-Phe-Cys-Gly-Ile-Lys-$Xaa_2$-Gly-Leu-Cys-Cys-Ser-Glu-Phe-Cys-Leu-Pro-Gly-Val-Cys-Pro-Gly ($Xaa_1$ or $Xaa_2$ is Pro or 4-trans-hydroxyproline) (SEQ ID NO:7). However, the other purified component did not yield a satisfactory mass spectrometric analysis. Since both components had the same sequence, it remained a possibility that these represented forms of the peptide with free carboxyl and amidated C-termini.

Example 6

Synthesis of δ-Conotoxin Peptide PVIA Sequence

The protected peptide resin was built using standard fmoc chemistry, couplings being carried out with equimolar amounts of amino acid derivative, DCC, and HOBT. All amino acids were purchased from Bachem (Torrence, Calif.), and the side chains were protected as follows: Hyp (t-Bu), Lys (boc), Ser (t-Bu), Tyr (t-Bu), Glu (t-Bu), and Thr (t-Bu). Cys residues 3, 17, 18 and 27 were protected by trt, while Cys residues 10 and 22 were protected by acm.

At the completion of synthesis, the terminal fmoc group was removed by standard treatment with piperidine/NMP (20% by volume). Peptide was removed from the resin by treatment for 2 h at 20° C. with $TFA/H_2O$/ethanedithiol/ phenol/thioanisole (90/5/2.5/7.5/5 by volume), and the whole mixture was filtered rapidly into tert-butyl methyl ether at −10° C. The pellet, almost free of ether, was dissolved in 60% acetonitrile containing 0.1% TFA.

A two-step oxidation protocol was used as described in Shon et al. (38) with a few minor changes. Crude linear peptide cleaved from 100 mg resin was directly subjected to oxidation in 20 mM FeCN in 0.1 Tris-acetate buffer (pH= 8.0) containing 60% acetonitrile. The peptide solution (diluted to 200 mL containing 60% acetonitrile) was dripped slowly (at least 30 min) into 200 mL of the FeCN solution in order to minimize any intermolecular disulfide bond formation. On average, 1 h is usually enough for complete oxidation. The oxidation reaction resulted in three bicyclic peptides with disulfide bonds among Cys 3, 17, 18 and 27. The three isomers were purified using a reversed-phase HPLC preparative column with a gradient of acetonitrile (27–50%) in 0.1% TFA and a flow rate of 20 mL/min. One of the three isomers gave native-like material after oxidation with 1 mM $I_2$ in 10% TFA and acetonitrile (5 min at room temperature, followed by a quench with 30 mM ascorbic acid).

In order to confirm the sequence assignment, and assess the functional effects of the presence or absence of C-terminal amidation, both the free and amidated forms of the peptide were synthesized and folded as described herein. Both synthetic peptides provided to be biologically active, the same in vivo symptomatology was induced by the synthetic forms and the native peptide purified from venom. The earlier eluting native lockjaw peptide peak exhibits the same retention time as the synthetic amidated peptide.

Example 7

Identification of DNA for δ-Conotoxin Peptide PVIA

A cDNA clone encoding the lockjaw peptide was purified from a library of *C. purpurascens* ω- and δ-conotoxin cDNAs using the lockjaw-specific oligonucleotide DHOG 538 (5' GARGCNTGYTAYGCNCC 3'; SEQ ID NO:8) as probe (36). The library was constructed in the pUC vector ptz18u by cloning PCR amplicons generated using reversed-transcribed *C. purpurascens* venom duct RNA (AMV reverse transcriptase, Boehringer Mannheim) and an oligonucleotide A corresponding to the signal sequence of ω- and δ-conotoxins and oligonucleotide poly(dT) as primers. Putative clones were sequenced using the Sequenase version 2.0 DNA sequencing kit and [$^{35}$S]dATP (Sequences version 2.0 seventh edition protocol).

The nucleotide sequence of the clone mad the inferred amino acid sequence for δ-conotoxin PVIA (lockjaw peptide) as shown in FIG. 1 are set forth in SEQ ID NO:9 and SEQ ID NO:10. The open reading frame encodes a typical signal sequence, with the prepropeptide organization found in other conotoxins (43). The precursor sequence has a typical conotoxin proteolytic cleavage site (36, 37). The predicted mature toxin sequence is identical to the peptide purified from venom, with a C-terminal amide group. The C-terminal -Cys-Phe-Gly-Gly-OH sequence (SEQ ID NO:11) of the precursor would be processed to a -Cys-Phe-Gly-$NH_2$ sequence by peptidylglycine α-amidating monooxygenase (44, 45).

Example 8

Assay Methods for GmVIA and MrVIA

Bioassays and Biological Activities. Local garden snails, *Helix aspersa*, weighing 3–5 g, were chosen for bioassays because they were readily available. In the presence of food, the snails became aroused and no longer stayed in the shells.

Once they were fully active and out of the shells, the snails were put on ice to slow down their activity. Under these conditions the heads tend to remain extended, allowing easy injection of 10–140 μL aliquots of toxin fractions. The injection, similar to intracranial injection in the common mouse bioassay (25), was near the cerebral ganglion where nerves are heavily localized. For comparison, intracranial injection into two-week old mice was done with doses of 20–60 nmol.

Electrophysiology. Isolated neurons from *Aplysia californica* or *Aplysia aculifera* were cultured as previously described (3, 26). The neurons were cultured at very low densities to prevent synaptic interactions among them. Passive and active membrane properties of the cultered neurons were studies using conventional intracellular recording and simulation techniques. Briefly, the cell body of a cultured neuron was impaled by a microelectrode filled with 2M KCl (4–10 MΩ resistance). The electrode was used for both current injection and voltage recordings. Analysis of the resting potential, input resistance, and action potential amplitude and shape was carried out in artificial sea water (ASW) composed of 460 mM NaCl, 10 mM KCl, 11 mM $CaCl_2$, 55 mM $MgCl_2$, an 10 mM HEPES, pH 7.6. The toxin for electrophysiological experiments was dissolved in ASW containing 10 mg/mL bovine serum albumin and was applied to the bathing solution to reach a final concentration of 0.3–0.75 μM.

Solutions. Control experiments were carried out in artificial sea water (ASW) composed of: 460 mM NaCl, 10 mM KCl, 11 mM $CaCl_2$, 55 mM $MgCl_2$ and 10 mM HEPES. The pH was adjusted to 7.6.

To minimize potassium currents, an external potassium channel blocking solution (PCBS) was used, in which KCl was substituted for by CsCl. In addition, the solution contained 50 mM tetraethylammonium chloride (TEA) and 0.1 mM 3,4-diaminopyridine (3, 4, DAP). The osmolarity of the solution was adjusted by reducing the NaCl concentration to 410 mM.

To monitor sodium current, a calcium-free PCBS solution was used. In this solution, $Ca^{2+}$ was substituted for by $Mg^{2+}$, and the solution was supplemented by 8 mM $Co^{2+}$ to prevent any $Ca^{2+}$ influx. For these experiments, the patch pipette contained: 440 CsCl, 40 CsGlutamate, 20 NaCl, 2 $MgCl_2$, 10 Ethyleneglycol-bis-(β-amino ethyl ether) N, N'-tetraacetic acid (BGTA), 100 N-[2-Hydroxyethyl] piperazine-N'[2-ethanesulfonic acid] (HEPES) and 3 adenosine-5-triphosphate ATP) (The values are in mM). The pH was adjusted to 7.3.

To monitor calcium currents, the external sodium ions were replaced by TEA. The patch pipette contained the same internal solution supplemented with 0.5 mM guanosine-5'-triphosphate (GTP) to slow the run-down of calcium channels (31). The pH was adjusted to 7.3.

Potassium containing external and internal solutions were used when outward currents were under study. Sodium currents were eliminated by replacing the sodium ions with Trizma 7.4 (Sigma, St. Louis). In these experiments, the patch pipette contained: 480 KCl, 20 NaCl, 2 $MgCl_2$, 10 EGTA, and 100 HEPES (values are in mM). The pH was adjusted to 7.3. Throughout, the ± sign stands for standard deviation of the mean.

Competitive Binding with ω-Conotoxin GVIA. The procedures for membrane preparation and binding assay were essentially as previously described by Cruz and Olivera (27), except that NaCl was used instead of choline chloride in the wash medium of the binding assay. Different concentrations of the peptide and ω-conotoxin GVIA were preincubated with the membrane preparation for 30 minutes on ice before the addition of $^{125}$I-labeled GVIA.

Example 9

Biological Activity of δ-Conotoxin Peptide GmVIA

Because *C. gloriamaris* is believed to be a snail-hunting cone, the initial in vivo bioassay used local garden snails. Volumes of peptide solution between 10 and 40 μL were injected in the head region, near the cerebral ganglion. Injection of approximately 20 nmol of purified δ-conotoxin GmVIA induced retraction of the head and body into the shell; this was followed by secretion of viscous green slime and a convulsive undulation into and out of the shell. Biological effects on garden snails were detectable at a dose of 1.25 nmol/g and very obvious at 2 nmol/g. No apparent biological activity was observed when a much greater dose of peptide (10 nmol/g) was injected peritoneally into mice.

Electrophysiology. A preliminary study of the electrophysiological effects of purified toxin was carried out on isolated Aplysia neurons. Changes in the resting potential, input resistance and action potential amplitude and shape upon addition of the toxin were assessed. The purified toxin revealed significant effects at final concentrations of 0.3–0.75 μM. Within 10–60 seconds after bath application of the toxin, quiescent neurons fired spontaneously. Concomitantly, the action potential duration increased by 1–2 orders of magnitude, extending in many experiments to over 250 ms. The changes in membrane excitability and action potential duration induced by the toxin were completely reversible upon washing of the neuron with ASW.

Toxin-induced prolongation of the action potential was still observed when $K^+$ and $Ca^{2+}$ conductances were blocked, suggesting that GmVIA's effect is most likely due to a decrease in the rate of sodium current inactivation. For instance, in the experiment in which $K^+$ conductances were blocked by using ASW in which KCl was replaced by $CaCl_2$. In addition, the solution contained 50 nM tetraethylammonium chloride and 0.1 mM 3,4-diaminopyridine (osmolarity of the solution was restored by reducing the NaCl concentration to 410 nM). We refer to this solution as potassium conductance blocking solution, or PCBS. Under these conditions, bath application of 0.5 μM toxin prolonged the spike duration. In the presence of the toxin and PCBS, bath application of $Ca^{2+}$ to block $Ca^{2+}$ current (final concentration of 8 mM) increased spike duration even further. This is most likely due to blockage of residual $Ca^{2+}$-dependent $K^+$ conductances, which contribute to the repolarization of the action potential.

These observations, together with preliminary whole-cell patch-clamp studies which were performed, indicate that the mechanism underlying the toxin effect is a slowing down of sodium current inactivation, rather than changes in $Ca^{2+}$ or $K^+$ currents.

Action potential broadening by bath application of 0.4 μM δ-conotoxin GmVIA was observed. The altered action potential is composed of an early peak, followed by a long plateau of somewhat lower amplitude. This broadening could be accounted for by several mechanisms, including the reduction of potassium conductances, an increase in the calcium or sodium conductances, or the activation of some latent calcium or sodium voltage gated channels.

To differentiate among these possibilities, experimental protocols that permitted examination of the isolated macroscopic currents of either $K^+$, $Ca^{2+}$ or $Na^+$ were used.

Whether the toxin alters the potassium currents was first analyzed. To that end, the sodium and calcium currents were blocked as previously described. In one experiment, the neuron was depolarized for 250 ms from a holding potential of −50 mV to various values. Application of δ-conotoxin GmVIA, at a final concentration of 0.5–2 μM, did not alter the potassium current-voltage elations, nor its kinetics (n=4).

Whether the toxin alters calcium currents was next analyzed. For these experiments (n=4), the sodium and potassium currents were blocked as previously described; and as in (29). In an experiment, the neuron was depolarized from a holding potential of −50 mV to various potentials. In this experiment, as well as in others of the same kind, a reduction of 10–20% in the amplitude of the calcium current was noticed during the experiment (lasting 20–60 minutes), but the normalized current voltage relationship of $Ca^{2+}$ was not altered. The reduction in the peak calcium current is most likely due to partial rundown of $Ca^{2+}$ channels (31), as a similar gradual decrease in the calcium current was also observed during the control periods. Thus, it appears that neither a reduction in potassium currents nor an increase in the duration of the calcium current can account for the effects of the toxin on spike shape.

To examine the effects of the toxin on the sodium current, a series of experiments (n=22) was performed in which the potassium currents and calcium currents were eliminated as previously described.

The voltage clamp records (in an experiment in which the minimal current was evoked by a depolarizing voltage clamp step from a holding potential of −50 mV to 22 mV) show that 0.5 μM δ-conotoxin GmVIA does not alter the rise time of the sodium current but slows the rate of sodium current inactivation. In the presence of the toxin, the sodium current inactivation is composed of two phases, an early phase which is slowed down in respect to the control and a second phase, which does not appear in control records altogether. This phase does not completely inactivate by the end of the voltage trace. In this and other experiments (n=8) in which $Ca^{2+}$ and $K^+$ currents were blocked, the decay of the sodium current in the control experiments was exponential, with a single time constant τ=0.35 ms (average τ=0.47±0.14 ms, n=8). Following the application of δ-conotoxin GmVIA, the rate of sodium current inactivation decreased and was clearly composed of two phases. The semi-log plot of the inactivation phase shows that from about 10 ms onwards, the inactivation time constant was 359.6 ms (average τ=488±120 ms, n=8). The inactivation rate of the early phase, obtained by subtracting the extrapolated slope from the slope of the earlier phase of the sodium current, increased from 0.35 ms in control to 0.84 ms (average of 0.86±0.12 ms, n=8) after application of δ-conotoxin GmVIA. While the inactivation rate of the sodium current was altered, the current voltage relationship of the early sodium current was not changed.

δ-Conotoxin GmVIA (0.5 μM) changed the steady-state voltage inactivation of the sodium channels. For this experiment, the holding potential ($V_h$) was set at various values ranging from −90 to 0 in V for 2 seconds. Sodium currents were generated by stepping the voltage to 22 mV for 15 minutes in $Ca^{2+}$-free PCBS and 8 mM $Co^{2+}$. The peak of early sodium conductance ($G_{Na+}$) was plotted as a function of the maximal sodium conductance ($G_{Na+}/G_{Na+max}$) observed when $V_h$ was −50 mV. The solid line shows: $G_{Na+}/G_{Na+max} = \{1+\exp[(V_h-V_{0.5})/S]\}^{-1}$, where $V_{0.5}$ is the half-inactivating voltage, and S is the slope parameter fitting the experimental data. Following bath application of the toxin, the inactivation curve shifted to more positive potentials and $V_{0.5}$ was −21 mV, compared with the value in control in which $V_{0.5}$=30 mV. The slopes of the inactivation curve in control and δ-conotoxin GmVIA treated neuron were the same (slope parameter=4.6).

It is interesting that steady state voltage inactivation of the slow inactivating phase of sodium current behaves precisely as the early phase of sodium current.

Activation of the early and late sodium current as a fraction of the maximal sodium conductance was analyzed. To determine the inactivation of the early sodium current in control experiments and in the presence of δ-conotoxin GmVIA, the membrane potential was set to −50 mV and then clamped for 0.5 minutes to various potentials ranging from −40 to 60 mV, in 5 mV increments. The resulting tail currents were measured and expressed as relative conductances. The activation curve of the slowly inactivating current was determined only in the presence of the toxin. This was done by setting the holding voltage to −50 mV and then clamping the membrane potential to various values (from −40 to 60 mV) for a duration of 15 minutes. The resulting tail current under these conditions consisted only of the slowly-inactivating phase, since the early sodium current was inactivated. The peak of the early sodium conductance and the peak of the late slowly inactivating conductance ($G_{Na+}$) were plotted as a function of the maximal sodium conductance $G_{Na+}/G_{Na+max}$) observed when $V_m$ was mV. The solid line shows: $G_{Na+}/G_{Na+max}=\{1=\exp[-(V_m-V_{0.5})/S]\}^{-1}$, where $V_m$ is the testing potential, $V_{0.5}$ is the half-activating voltage and S is the slope parameter fitting the experimental data. Following bath application of 0.4–0.7 μM toxin, the activation curve of the early sodium current is shifted to more negative potentials, and $V_{0.5}$ was 10 mV compared to the value in control where $V_{0.5}$=15 mV. The V0.5 of late sodium current is 4 mV. The slopes of the activation curves in control and δ-conotoxin GmVIA treated neurons (the early sodium current and the late sodium current) are the stone (slope parameter=4.75).

The relative refractory period of the early and the slowly inactivating phases of the sodium currents were studied by delivering two consecutive depolarizing voltage clamp pulses to the neuron. The first depolarizing pulse lasted for 10 minutes and the second for 25 minutes, the time interval between the two pulses was gradually reduced, and the sodium currents were monitored in control and following toxin application. Prior to application of the toxin (0.5 μM), both pulses evoked the early inactivating sodium currents. The amplitude of the sodium current induced by the second pulse decreased as the time interval between the two pulses was reduced. Toxin application induced the appearance of the slowly inactivating phases of the sodium current not seen in the control. The amplitude of the slowly inactivating sodium current was almost constant independent of the time interval between the first and second voltage clamp pulses. It was also interesting to note that the amplitude of the slowly inactivating sodium current is independent of the amplitude of the early sodium current.

Comparison Between Effects of δ-Conotoxin GmVIA and δ-Conotoxin TxVIA. The electrophysiological effects of δ-conotoxin GmVIA mad TxVIA isolated from another mollusc hunting-snail *Conus textile* on cultured Aplysia neurons (3, 32) were quite similar. Both toxins induced action potential broadening and increased excitability by slowing the rate of sodium current inactivation with no significant effects on either the rise time or the peak of the voltage-activated sodium current. However, there were differences between the effects of these two toxins. For this experiment (n=5), potassium and calcium currents were eliminated and the neuron was clamped from a holding potential of −50 mV to 22 mV. The effects of the two peptides were studied sequentially on the same neuron. First, the neuron was exposed to 0.5 μM GmVIA, then thoroughly washed until the sodium current recovered to control levels. TxVIA was then applied and induced a prolongation of the sodium current. The superimposed traces clearly demonstrated that δ-conotoxin GmVIA induced a much longer slowly inactivating phase of the sodium current than δ-conotoxin TxVIA. Similar observations were made when the order of toxin application was reversed. The differences in the inactivation kinetics of the sodium current are not due to differences in the affinities of the two toxins for the sodium channels, since exposure, of the neurons to higher concentrations of δ-conotoxin TxVIA never altered the duration of the slowly inactivating current to the same extent as did δ-conotoxin GmVIA.

Competitive Binding with ω-Conotoxin GVIA. At concentrations up to 5.0 μM of the test peptide, δ-conotoxin GmVIA did not compete with $^{125}$I-labeled ω-conotoxin GVIA on brain membrane preparations from frogs, chicks and rats. Positive controls with unlabelled ω-conotoxin GVIA gave the expected level of competition: 25 nM unlabelled toxin displaced approximately 90% of $^{125}$I-GVIA, and 250 nM competed out approximately 98% of label.

Discussion. δ-Conotoxin GmVIA, the major component present in the venom of the mollusc hunting snail *Conus gloriamaris*, elicits spike broadening at concentration of 5 μM. Voltage clamp analysis reveals that the effects of the toxin are expressed by: Slowing down the rate of the early sodium current inactivation; induction of a late slowly inactivating sodium current which is not detectable in control experiments; Shifting the steady state sodium current inactivation curve to more depolarized values and shifting the activation curve to more hyperpolarized values. These changes are not associated with an increase in the rate of rise of the early sodium current or by a change in the peak sodium current.

The experiments show that the toxin modifies the sodium current inactivation kinetics from a single exponential with an average τ=0.47±0.14 minutes to a slower decay, which can be described by two time constants: the initial inactivation phase has a τ=0.86±0.12 minute and the second phase a τ=488±120 minutes. These changes in time constants may account for the typical alterations in the action potential shape induced by δ-conotoxin GmVIA. In ASW and in the presence of the toxin, the early fast phase of the action potential and its plateau corresponds to the early rapidly inactivating sodium current and the long-lasting slowly inactivating phase.

The amplitude of the late phase of the sodium current induced by δ-conotoxin GmVIA is independent of the amplitude of the early current. Thus, even when the early current is completely inactivated by a prepulse, the amplitude of the late component is not reduced. The simplest explanation to account for this observation is that the toxin alters the inactivation kinetics of the entire population of sodium channels from a single time constant to dual time constants. If this assumption is right, then the observations suggest that in the presence of δ-conotoxin-GmVIA, the sodium channels can be activated in two modes: In the one mode they go through the rapid inactivation phase to the slow inactivating phase, or alternatively are "switched" directly into the slowly inactivating mode without first going through the rapidly inactivating phase. An alternative explanation assumes that the toxin activates a population of silent, slowly inactivating sodium channels. This hypothesis is also consistent with the finding that the non-inactivating phase can be activated independently of the early sodium current. However, since the peak of the early sodium current is not increased in the presence of the toxin as would be expected if additional sodium channels were activated, then this hypothesis seems to be less likely.

The macroscopic effects of the toxin purified from the venom of the shallow water mollusc hunting snail *C. textile* (3) and the one purified from the deep water *C. gloriamaris*, are similar but not identical. Both toxins alter the inactivation kinetics of the sodium current from a process that is best described by a single exponent into a biphasic process. However, the effects of the two toxins differ because δ-conotoxin GmVIA induces a significantly longer, slow inactivation phase than that induced by δ-conotoxin TxVIA. Additionally, the effects of δ-conotoxin TxVIA undergo desensitization in the presence of the toxin, whereas the effects of δ-conotoxin GmVIA are observed for as long as the toxin is present in the bathing solution. It is reasonable to assume that these peptide toxins target the same ligand binding pocket of the sodium channel: Both peptides are extremely hydrophobic, a characteristic which may be important for binding to this specific site. Nevertheless, the differences in the primary sequences of these peptides cause a clear difference in their detailed effects on sodium current inactivation kinetics.

Example 10

Biological Activity of μO-Conotoxin Peptide MrVIA

Blockade of Action Potential and Inward Sodium Current by μO-Conotoxin MrVIA as Revealed by Current and Voltage Clamp Experiments. The current clamp experiments were carried out by a microelectrode inserted into the cell body of a cultured Aplysia neuron. The electrode was used for both current injection and voltage recording. To minimize the potassium conductances, the current clamp experiments were carried out in artificial sea water containing 50 mM tetraethylammonium chloride (TEA) and 0.3 mM 3,4-diaminopyridine (3,4-DAP) (3). ($A_1$) control: The action potential was generated by an intracellular rectangular depolarizing pulse. ($A_2$): Ten seconds after toxin application to reach a final bath concentration of 350 nM, the action potential was blocked. An increase in the stimulus intensity after the blockade of the action potential failed to elicit a regenerative response. To directly examine the toxin action on sodium, calcium and potassium currents, the whole-cell patch clamp configuration was used. Adequate space clamp was achieved by trimming off the main axon of the neuron prior to the experiment (33, 34). To monitor only the sodium current ($I_{Na+}$), the patch clamp experiments were carried out in an external solution composed of: 410 NaCl, 10 CsCl, 66 $MgCl_2$, 9 $CoCl_2$, 50 TEA, 0.3 3,4-DAP. The path electrode contained 440 CsCl, 40 CsGlutamate, 20 NaCl, 2 $MgCl_2$, 10 EGTA, 100 HEPES and 3 ATP (the values are given in mM). The inward $I_{Na+}$ evoked by depolarizing the neuron from a holding potential of −50 to 20 mV was completely blocked 30 seconds following the application of 250 nM MrVIA. Partial blockage of $I_{Na+}$ by 40 nM toxin revealed that the block is not associated with a change in the current voltage relationships. Patch clamp experiments revealed that calcium and potassium currents are not affected by the toxin.

The μO precursor sequence can be readily aligned with the precursor sequences of ω-conotoxin GVIA (36) as well as with δ-conotoxin TxVIA from *Conus textile* (37). Extensive sequence identity between the μO-, ω- and δ-conotoxin precursors is observed. Although structurally related, the peptides are functionally divergent. Binding competition experiments demonstrate that competitive binding inhibition by μO-conotoxin MrVIA does not occur for the high affinity ω-conotoxin GVIA binding site on mammalian brain $Ca^{2+}$ channels. Electrophysiological experiments show that μO-conotoxin MrVIA and δ-conotoxin TxVIA elicit opposite effects, since δ-conotoxin TxVIA is an excitotoxin which increases $Na^+$ conductance (3). Thus, although μO-, ω- and δ-conotoxins apparently belong to the stone protein superfamily, they have strikingly different physiological effects. In contrast, the functionally homologous μ-conotoxin GIIIA has an unrelated disulfide structure, and its precursor sequence shows no homology whatsoever to the μO-conotoxins from *C. marmoreus*. Thus, the peptides provide molecular guideposts for species diversification in this genus. The genetic analysis shows that the μO-conotoxins, Na channel inhibitors from *C. marmoreus*, were independently evolved from the μO-conotoxins from fish-hunting Conus. Thus, in this single genus, one protein superfamily comprises multiple functionally-distinct toxin classes, but functional convergence of two sodium channel-blocking toxins from different superfamilies is also observed.

In *Conus textile* venom one peptide, δ-conotoxin TxVIA, is present at higher levels than any other (27). The purified δ-conotoxin induces the convulsive contractures in snails observed with whole *C. textile* venom. In contrast, μO-conotoxin MrVIA causes the flaccid relaxation characteristic of crude *C. marmoreus* venom. Thus, the two peptides, both major components of their respective venoms, are likely to play key roles in the contrasting physiological strategy that these two snail-hunting Conus adopt to cause immobilization outside the shell. The two peptides target the same macromolecular complex (the voltage-sensitive sodium channel) but *Conus textile* increases excitability by inhibiting channel inactivation through its δ-conotoxin while *Conus marmoreus* decreases excitability by blocking channel conductance via its μO-conotoxin.

Example 11

Assay Methods for δ-Conotoxin PVIA

Biological Assays. Goldfish (1.0–1.5 g) were injected into the intraperitoneal cavity, and 10–14 day-old Swiss Webster mice were injected intracranially (25). The garden snail *Helix aspersa* was injected into the head as described (38).

Electrophysiology. The cutaneus pectoris muscle of the leopard frog *Rana pipiens* was prepared and placed in a recording chamber as previously described (39) except that the muscle was not pretreated with any toxins or drugs unless otherwise indicated. The motor nerve was electrically stimulated every 30 s with a rectangular suprathreshold pulse lasting 0.1 ms, and extracellular recording electrodes were used to monitor the compound action potential from the muscle.

Membrane Preparation. The crude membrane fraction was obtained from the whole brain of 6–8 month-old Sprague-Dawley rats as previously described (40).

Radiolabeling of Conotoxins. Iodination of δ-conotoxin TxVIA was carried out using the water-soluble reagent chloramine T. Two nanomoles of δ-conotoxin TxVIA dissolved in 50% acetonitrile in water was incubated for 10 min at room temperature with 2 nmol $Na^{125}I$ (1.1 mCi/nmol) and 10 nmol of chloramine T in 200 mM Tris (pH 8.6). The reaction was quenched with 50 μL of 500 mM ascorbic acid and 50 μL of 200 mM methionine, and the solution was gently extracted twice with 500 μL of diethyl ether. Upon application onto an $C_{18}$ analytical column (Vydac), the monoiodinated TxVIA eluted shortly after the unmodified δ-conotoxin TxVIA at approximately 56% acetonitrile on a linear gradient of acetonitrile (36–63%). The label was stored as a HPLC effluent at −20° C. with 57 mM methionine and centrifuged before use in binding assays. ω-Conotoxin GVIA was labeled by resuspending 10 nmol of peptide in 0.1% TFA, adding an equal volume of 0.25M Tris-HCl, pH 7.0, and incubating with an equivalent amount of chloramine T and 4 nmol of $Na^{125}I$ (2.2 mCi/nmol) for 10 min at room temperature. The $[^{125}I]\omega$-GVIA was purified by HPLC as previously described (40, 41).

Competitive binding Assays. Two assay procedures were used. The first was optimized for $[^{125}I]\delta$-conotoxin TxVIA binding (42). The second conditions were standard ω-conotoxin binding assays (42), modified by adding 130 mM NaCl, 5 mM $CaCl_2$, 1.3 mM KCl and 0.8 mM $MgCl_2$ to the assay mix.

Example 12

Biological Activity of δ-Conotoxin Peptide PVIA

Electrophysiology. The effects of the lockjaw peptide on a flog neuromuscular junction preparation were examined. Clearly, neuromuscular transmission was not blocked by the lockjaw peptide; instead trains of action potentials were produced in response to a single nerve stimulus when the preparation was exposed to toxin. The effects of the toxin were reversible. The experiment was performed six times and in every case repetitive action potentials were observed. The number of action potentials produced by stimulation increased with time of exposure to the toxin. The results provide a plausible explanation for the fish lockjaw syndrome; in effect, repetitive action potentials in the fish jaw musculature elicited by the lockjaw peptide would result in a titanic paralysis and the rigid extension of the fish mouth part.

Competitive Binding with ω-Conotoxin GVIA. The arrangement of cysteine residues in the lockjaw peptide is characteristic of the so-called "four-loop" family of Conus peptides. In fish-hunting cones, the major peptide family with the four-loop Cys motif is the ω-conotoxins, which inhibit voltage-sensitive Ca channels (1). Indeed, when the sequence of the lockjaw peptide precursor is aligned with the precursor sequence of an ω-conotoxin, considerable identity is observed (FIG. 1). For this reason, the purified lockjaw peptide was tested for binding to the ω-conotoxin site. In a competition binding experiment using $^{125}I$-radiolabeled GVIA, no displacement of specific ω-conotoxin binding (see Table 1) was found, suggesting that the lockjaw peptide is not a member of the ω-conotoxin family.

TABLE 1

Binding Competition Experiments

|  | $[^{125}I]\delta$-TxVIA label (cpm bound) | $[^{125}I]\omega$-GVIA label (cpm bound) |
| --- | --- | --- |
| no additions | 4890 ± 691 | 4405 ± 123 |
| δ-Conotoxin TxVIA | 925 ± 39 | 4719 ± 40 |
| ω-conotoxin GVIA | 4710 ± 450 | 954 ± 209 |

TABLE 1-continued

Binding Competition Experiments

|  | $[^{125}I]\delta$-TxVIA label (cpm bound) | $[^{125}I]\omega$-GVIA label (cpm bound) |
| --- | --- | --- |
| δ-conotoxin PVIA (amidated) | 889 ± 92 | 4927 ± 253 |
| δ-conotoxin PVIA (nonamidated) | 848 ± 196 | 4393 ± 458 |

Binding Evidence That the Lockjaw Peptide is a δ-Conotoxin. The C. purpurascens peptide exhibits an even greater similarity to the precursor sequence of a previously characterized peptide from a snail-hunting Conus venom, δ-conotoxin TxVIA (37). The δ-conotoxins were previously shown to bind specifically to voltage sensitive Na channels (46), causing a delay in channel inactivation resulting in an increase in Na conductance (3; 38). The sequence homology in FIG. 1 strongly suggested that the lockjaw peptide might be a member of the δ-conotoxin family.

In order to confirm whether the C. purpurascens peptide was in fact a δ-conotoxin, binding competition was performed using radiolabeled δ-conotoxin TxVIA as the probe for high-affinity sites on rat brain Na channel (29). The results are shown in Table 1 above. It is clear that the peptide completely displaced specific δ-conotoxin TxVIA binding under assay conditions where there was not detectable displacement of ω-conotoxin GVIA binding. The experiments in Table 1 were carried out under conditions optimal for δ-conotoxin TxVIA binding; even under assay conditions optimal for ω-conotoxin GVIA binding, the lockjaw peptide displaced the δ-conotoxin but not $[^{125}I]\omega$-GVIA. These results, together with the precursor sequence homologies, support the conclusion that the C. purpurascens peptide targets to the δ-conotoxin binding site on Na channels and is not an ω-conotoxin. The initially seen electrophysiological effects are thus rationalized by the lockjaw peptide increasing voltage-gated $Na^+$ currents (47), thereby making the neuromuscular junction more electrically excitable.

In vivo Experiments. The molecular genetic and binding data which indicate that the lockjaw peptide is a δ-conotoxin and not an ω-conotoxin are reinforced by the observed in vivo biological activity of the peptide on fish and mice. The ω-conotoxins cause a characteristic shaking syndrome when injected intracranially into mice. In contrast, injection of 0.5 nmol of the purified lockjaw peptide caused hyperactivity, rapid running, limb extension, and death. At higher doses (≈5 nmol), the peptide was remarkably toxic in mice, causing death in 10 s. Thus, the peptide is a potent excitotoxin in mammals, a result consistent with Na channel-targeted ligand, which increases conductance, rather than a calcium channel blocker of the δ-conotoxin class.

In fish, the peptide elicited spurts of rapid swimming, with twisted motions, quivering fins, and the lockjaw extended mouth syndrome. Rigid paralysis and death were observed if 0.5–5.0 nmol was injected.

Previously characterized δ-conotoxins were highly potent in all molluscs tested (28, 47, 29, 38). The peptide from C. purpurascens was injected into a mollusc. In contrast to the results with δ-conotoxins GmVIA and TxVIA which cause typical "King-Kong type" symptomatology (28) in this snail, the lockjaw peptide elicited no detectable biological effects. Thus, the lockjaw peptide is a potent toxin in vertebrate systems but is inactive in this mollusc.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

1. Myers, R. A. et al. (1993). Conus Peptides as Chemical Probes for Receptors and Ion Channels. *Chem. Rev.* 93:1923–1936.
2. Miljanich, G. P. et al. (1993). U.S. Pat. No. 5,264,371.
3. Hasson, A. et al. (1993). *Eur. J. Neurosci.* 5:56–64.
4. Olivera, B. M. et al. (1984). U.S. Pat. No. 4,447,356.
5. Sambrook, J. et al. (1979). *Molecular Cloning: A Laboratory Manual*, 2nd Ed., Cold Spring Harbor Laboratory, Cold Spring Harbor, N.Y.
6. Gray, W. R. (1993). Disulfide Structures of Highly Bridged Peptides: A New Strategy for Analysis. *Protein Science* 2:1732–1748.
7. *Methoden der Organischen Chemie (Houben-Weyl): Synthese von Peptiden*, E. Wunsch (Ed.), Georg Thieme Verlag, Stuttgart, Ger. (1974).
8. Stewart and Young, *Solid-Phase Peptide Synthesis*, Freeman & Co., San Francisco, Calif. (1969).
9. Vale et al. (1978). U.S. Pat. No. 4,105,603.
10. U.S. Pat. No. 3,972,859 (1976).
11. U.S. Pat. No. 3,842,067 (1974).
12. U.S. Pat. No. 3,862,925 (1975).
13. Bodansky et al. (1966). *Chem. Ind.* 38:1597–98.
14. U.S. Pat. No. 4,569,967.
15. Horiki, K. et al. (1978). *Chemistry Letters* 165–68.
16. Schroder & Lubke (1965). *The Peptides* 1:72–75, Academic Press, N.Y.
17. Kapoor (1970). *J. Pharm. Sci.* 59:1–27.
18. Kaiser et al. (1970). *Anal. Biochem.* 34:595.
19. Rivier, J. R. et al. (1978). *Biopolymers* 17:1927–38.
20. Cruz, L. J. et al. (1976). Block of P-type calcium channels by the funnel web spider toxin ω-Aga-IVA. *Nature* 355:827–29.
21. Burns, J. A. et al. (1991). Selective reduction of disulfides by tris-[2-carboxyethyl]phosphine, *J. Org. Chem.* 56:2648–50.
22. Monje, V. D. et al. (1993). *Neuropharm.* 32:1149.
23. McIntosh, J. M. et al. (1994). *J. Biol. Chem.* 269:16733–16739.
24. McIntosh, J. M. et al. (1994) *Toxicon.* 32:1561–1564.
25. Olivera, B. M. et al. *Biochem.* 23:5087.
26. Schacher, S. and Proshansky, E. (1983). *J. Neurosci.* 3:2403
27. Cruz et al. (1986).
28. Hillyard, D. R. et al. (1989). *Biochem.* 28:358.
29. Fainzilber, M., et al. (1994). *J. Biol. Chem.* 269:2574–2580.
30. Brezine, V. et al. (1987). *J. Physiol. Lond.* 388:565–595.
31. Fox, A. P. et al. (1987). *J. Physiol. Lond.* 394:149–172
32. Spira, M. E. et al. (1993). *Isr. J. Med Sci.* 29:530–543.
33. Hamill, O. P. et al. (1981). Improved patch clamp techniques for high-resolution current reading from cells and cell-free membrane patches. *Pflügers Arch.* 391:85–100.
34. Benbassat, D. and Spira, M. E. (1993). *J. Exp. Neurol.* 122:295–300.
35. Spira, M. E. et al. (1993). *J. Neurobiol.* 24:300–316.
36. Colledge, J. C., et al. (1992). *Toxicon* 30:1111–1116.
37. Woodward, S. R., et al. (1990). *EMBO J.* 1:1015–1020.
38. Shon, K. -J., et al. (1994). *Biochemistry* 33:11420–11425
39. Yoshikami, D., et al. (1989). *Ann. N. Y. Acad. Sci.* 560:230–248.
40. Cruz, L. J. and Olivera, B. M. (1986). *J. Biol. Chem.* 361:6230–6233.
41. Cruz, L. J., et al. (1987). In *Integration and Control of Metabolic Processes. Pure and Applied Aspects*, Kon, O. L., ed., Cambridge University Press, Cambridge, pp. 95–102.
42. Hillyard, D. R., et al. (1992). *Neuron* 9:60–77.
43. Olivera, B. M., et al. (1990). *Science* 249:257–263.
44. Bradbury, A. F., et al. (1982). *Nature* 298:686–688.
45. Murthy, A. S. N., et al. (1987). *Mol. Endocrinol.* 1:290–299.
46. Fainzilber, M., et al. (1994). *Biochemistry* 33:9523–9529.
47. Fainzilber, M., et al. (1991). *Eur. J. Biochem.* 202:589–595.
48. Kobayashi, J., et al. (1982). *Biochem. Biophys. Res. Commun.* 105:1389–1395.

What is claimed is:

1. A substantially pure δ-conotoxin PVIA peptide having the formula Glu-Ala-Cys-Tyr-Ala-$Xaa_1$-Gly-Thr-Phe-Cys-Gly-Ile-Lys-$Xaa_2$-Gly-Leu-Cys-Cys-Ser-Glu-Phe-Cys-Leu-Pro-Gly-Val-Cys-Pro-Gly (SEQ ID NO:7), wherein $Xaa_1$ and $Xaa_2$ are independently Pro or 4-trans-hydroxyproline.

2. The peptide of claim 1 wherein $Xaa_1$ is 4-trans-hydroxyproline.

3. The peptide of claim 1 wherein $Xaa_1$ is Pro.

4. The peptide of claim 1 wherein $Xaa_2$ is 4-trans-hydroxyproline.

5. The peptide of claim 1 wherein $Xaa_2$ is Pro.

6. The peptide of claim 2 wherein $Xaa_2$ is Pro.

7. The peptide of claim 2 wherein $Xaa_2$ is 4-trans-hydroxyproline.

8. The peptide of claim 3 wherein $Xaa_2$ is Pro.

9. The peptide of claim 3 wherein $Xaa_2$ is 4-trans-hydroxyproline.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Conus gloriamaris
        ( B ) STRAIN: GmVIA ( i x ) FEATURE:
    ( A ) NAME/KEY: Disulfide-bond
    ( B ) LOCATION: 4..19

( i x ) FEATURE:
    ( A ) NAME/KEY: Disulfide-bond
    ( B ) LOCATION: 11..24

( i x ) FEATURE:
    ( A ) NAME/KEY: Disulfide-bond
    ( B ) LOCATION: 18..28

( x i ) SEQUENCE DESCRIPTION: SEQ ID NO:1:

```
Val Lys Pro Cys Arg Lys Glu Gly Gln Leu Cys Asp Pro Ile Phe Gln
 1               5                  10                  15

Asn Cys Cys Arg Gly Trp Asn Cys Val Leu Phe Cys Val
             20                  25
```

( 2 ) INFORMATION FOR SEQ ID NO:2:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Conus marmoreus ( i x ) FEATURE:
        ( A ) NAME/KEY: Modified-site
        ( B ) LOCATION: 3
        ( D ) OTHER INFORMATION: /note= "Xaa at residue 3 is Arg or
            Ser"

( i x ) FEATURE:
        ( A ) NAME/KEY: Modified-site
        ( B ) LOCATION: 14
        ( D ) OTHER INFORMATION: /note= "Xaa at residue 14 is Ile or
            Leu"

( i x ) FEATURE:
        ( A ) NAME/KEY: Modified-site
        ( B ) LOCATION: 17
        ( D ) OTHER INFORMATION: /note= "Xaa at residue 17 is Ile or
            Val"

( i x ) FEATURE:
        ( A ) NAME/KEY: Disulfide-bond
        ( B ) LOCATION: 2..20

( i x ) FEATURE:
        ( A ) NAME/KEY: Disulfide-bond
        ( B ) LOCATION: 9..25

( i x ) FEATURE:
        ( A ) NAME/KEY: Disulfide-bond
        ( B ) LOCATION: 19..30

( x i ) SEQUENCE DESCRIPTION: SEQ ID NO:2:

```
Ala Cys Xaa Lys Lys Trp Glu Tyr Cys Ile Val Pro Ile Xaa Gly Phe
 1               5                  10                  15

Xaa Tyr Cys Cys Pro Gly Leu Ile Cys Gly Pro Phe Val Cys Val
             20                  25                  30
```

( 2 ) INFORMATION FOR SEQ ID NO:3:

( i ) SEQUENCE CHARACTERISTICS:

(A) LENGTH: 31 amino acids
(B) TYPE: amino acid
(C) STRANDEDNESS: single
(D) TOPOLOGY: linear (i i) MOLECULE TYPE: peptide (i i i) HYPOTHETICAL: NO (i v) ANTI-SENSE: NO (v i) ORIGINAL SOURCE:
(A) ORGANISM: Conus marmoreus
(B) STRAIN: MrVIA (i x) FEATURE:
(A) NAME/KEY: Disulfide-bond
(B) LOCATION: 2..20

(i x) FEATURE:
(A) NAME/KEY: Disulfide-bond
(B) LOCATION: 9..25

(i x) FEATURE:
(A) NAME/KEY: Disulfide-bond
(B) LOCATION: 19..30

(x i) SEQUENCE DESCRIPTION: SEQ ID NO:3:

Ala Cys Arg Lys Lys Trp Glu Tyr Cys Ile Val Pro Ile Ile Gly Phe
1               5                   10                  15
Ile Tyr Cys Cys Pro Gly Leu Ile Cys Gly Pro Phe Val Cys Val
            20                  25                  30

(2) INFORMATION FOR SEQ ID NO:4:

(i) SEQUENCE CHARACTERISTICS:
(A) LENGTH: 31 amino acids
(B) TYPE: amino acid
(C) STRANDEDNESS: single
(D) TOPOLOGY: linear (i i) MOLECULE TYPE: peptide (i i i) HYPOTHETICAL: NO (i v) ANTI-SENSE: NO (v i) ORIGINAL SOURCE:
(A) ORGANISM: Conus marmoreus
(B) STRAIN: MrVIB (i x) FEATURE:
(A) NAME/KEY: Disulfide-bond
(B) LOCATION: 2..20

(i x) FEATURE:
(A) NAME/KEY: Disulfide-bond
(B) LOCATION: 9..25

(i x) FEATURE:
(A) NAME/KEY: Disulfide-bond
(B) LOCATION: 19..30

(x i) SEQUENCE DESCRIPTION: SEQ ID NO:4:

Ala Cys Ser Lys Lys Trp Glu Tyr Cys Ile Val Pro Ile Leu Gly Phe
1               5                   10                  15
Val Tyr Cys Cys Pro Gly Leu Ile Cys Gly Pro Phe Val Cys Val
            20                  25                  30

(2) INFORMATION FOR SEQ ID NO:5:

(i) SEQUENCE CHARACTERISTICS:
(A) LENGTH: 255 base pairs
(B) TYPE: nucleic acid (C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Conus marmoreus
(B) STRAIN: MrVIB (ix) FEATURE:
(A) NAME/KEY: CDS
(B) LOCATION: 1..246

(ix) FEATURE:
(A) NAME/KEY: sig_peptide
(B) LOCATION: 1..66

(ix) FEATURE:
(A) NAME/KEY: mat_peptide
(B) LOCATION: 154..246

(xi) SEQUENCE DESCRIPTION: SEQ ID NO:5:

| ATG | AAA | CTG | ACG | TGC | ATG | ATG | ATC | GTT | GCT | GTG | CTG | TTC | TTG | ACA | GCC | 48 |
|---|---|---|---|---|---|---|---|---|---|---|---|---|---|---|---|---|
| Met | Lys | Leu | Thr | Cys | Met | Met | Ile | Val | Ala | Val | Leu | Phe | Leu | Thr | Ala | |
| -51 | -50 | | | | -45 | | | | | | -40 | | | | | |

| TGG | ACG | CTC | GTC | ATG | GCT | GAT | GAC | TCC | AAC | AAT | GGA | CTG | GCG | AAT | CAT | 96 |
|---|---|---|---|---|---|---|---|---|---|---|---|---|---|---|---|---|
| Trp | Thr | Leu | Val | Met | Ala | Asp | Asp | Ser | Asn | Asn | Gly | Leu | Ala | Asn | His | |
| -35 | | | | | -30 | | | | | -25 | | | | | -20 | |

| TTT | TTG | AAA | TCA | CGT | GAC | GAA | ATG | GAG | GAC | CCC | GAA | GCT | TCT | AAA | TTG | 144 |
|---|---|---|---|---|---|---|---|---|---|---|---|---|---|---|---|---|
| Phe | Leu | Lys | Ser | Arg | Asp | Glu | Met | Glu | Asp | Pro | Glu | Ala | Ser | Lys | Leu | |
| | | | | -15 | | | | | -10 | | | | | -5 | | |

| GAG | AAA | AGG | GCG | TGC | AGC | AAA | AAA | TGG | GAA | TAT | TGT | ATA | GTA | CCG | ATC | 192 |
|---|---|---|---|---|---|---|---|---|---|---|---|---|---|---|---|---|
| Glu | Lys | Arg | Ala | Cys | Ser | Lys | Lys | Trp | Glu | Tyr | Cys | Ile | Val | Pro | Ile | |
| | | | 1 | | | | 5 | | | | | 10 | | | | |

| CTT | GGA | TTC | GTA | TAT | TGC | TGC | CCT | GGC | TTA | ATC | TGT | GGT | CCT | TTC | GTC | 240 |
|---|---|---|---|---|---|---|---|---|---|---|---|---|---|---|---|---|
| Leu | Gly | Phe | Val | Tyr | Cys | Cys | Pro | Gly | Leu | Ile | Cys | Gly | Pro | Phe | Val | |
| | 15 | | | | | 20 | | | | | 25 | | | | | |

| TGC | GTT | TGATAGTGA | | | | | | | | | | | | | | 255 |
|---|---|---|---|---|---|---|---|---|---|---|---|---|---|---|---|---|
| Cys | Val | | | | | | | | | | | | | | | |
| 30 | | | | | | | | | | | | | | | | |

(2) INFORMATION FOR SEQ ID NO:6:

(i) SEQUENCE CHARACTERISTICS:
(A) LENGTH: 82 amino acids
(B) TYPE: amino acid
(D) TOPOLOGY: linear (ii) MOLECULE TYPE: protein (xi) SEQUENCE DESCRIPTION: SEQ ID NO:6:

| Met | Lys | Leu | Thr | Cys | Met | Met | Ile | Val | Ala | Val | Leu | Phe | Leu | Thr | Ala |
|---|---|---|---|---|---|---|---|---|---|---|---|---|---|---|---|
| -51 | -50 | | | | -45 | | | | | | -40 | | | | |

| Trp | Thr | Leu | Val | Met | Ala | Asp | Asp | Ser | Asn | Asn | Gly | Leu | Ala | Asn | His |
|---|---|---|---|---|---|---|---|---|---|---|---|---|---|---|---|
| -35 | | | | | -30 | | | | | -25 | | | | | -20 |

| Phe | Leu | Lys | Ser | Arg | Asp | Glu | Met | Glu | Asp | Pro | Glu | Ala | Ser | Lys | Leu |
|---|---|---|---|---|---|---|---|---|---|---|---|---|---|---|---|
| | | | | -15 | | | | | -10 | | | | | -5 | |

| Glu | Lys | Arg | Ala | Cys | Ser | Lys | Lys | Trp | Glu | Tyr | Cys | Ile | Val | Pro | Ile |
|---|---|---|---|---|---|---|---|---|---|---|---|---|---|---|---|
| | | | 1 | | | | 5 | | | | | 10 | | | |

| Leu | Gly | Phe | Val | Tyr | Cys | Cys | Pro | Gly | Leu | Ile | Cys | Gly | Pro | Phe | Val |
|---|---|---|---|---|---|---|---|---|---|---|---|---|---|---|---|
| | 15 | | | | | 20 | | | | | 25 | | | | |

| Cys | Val |
|---|---|
| 30 | |

(2) INFORMATION FOR SEQ ID NO:7:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Conus purpurascens (ix) FEATURE:
        (A) NAME/KEY: Modified-site
        (B) LOCATION: 6
        (D) OTHER INFORMATION: /note= "Xaa at residue 6 is Pro or
            4-trans- hydroxyproline"

(ix) FEATURE:
        (A) NAME/KEY: Modified-site
        (B) LOCATION: 14
        (D) OTHER INFORMATION: /note= "Xaa at residue 14 is Pro or
            4-trans- hydroxyproline"

(xi) SEQUENCE DESCRIPTION: SEQ ID NO:7:

```
Glu Ala Cys Tyr Ala Xaa Gly Thr Phe Cys Gly Ile Lys Xaa Gly Leu
 1               5                  10                  15
Cys Cys Ser Glu Phe Cys Leu Pro Gly Val Cys Pro Gly
            20                  25
```

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA PRIMER"

(iii) HYPOTHETICAL: YES (iv) ANTI-SENSE: NO (vi) ORIGINAL SOURCE:
        (A) ORGANISM: Conus purpurascens (xi) SEQUENCE DESCRIPTION: SEQ ID NO:8:

GARGCNTGYT AYGCNCC                   17

(2) INFORMATION FOR SEQ ID NO:9:

(i) SEQUENCE CHARACTERISTICS:
        (A) LENGTH: 243 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Conus purpurascens ( i x ) FEATURE:
  ( A ) NAME/KEY: CDS
  ( B ) LOCATION: 1..243

( i x ) FEATURE:
  ( A ) NAME/KEY: sig_peptide
  ( B ) LOCATION: 1..66

( i x ) FEATURE:
  ( A ) NAME/KEY: mat_peptide
  ( B ) LOCATION: 154..243

( x i ) SEQUENCE DESCRIPTION: SEQ ID NO:9:

| ATG | AAA | CTG | ACG | TGC | GTG | ATG | ATC | GTT | GCT | GTG | CTG | TTC | TTG | ACT | GCC | 48 |
|---|---|---|---|---|---|---|---|---|---|---|---|---|---|---|---|---|
| Met | Lys | Leu | Thr | Cys | Val | Met | Ile | Val | Ala | Val | Leu | Phe | Leu | Thr | Ala | |
| -51 | -50 | | | | | -45 | | | | | -40 | | | | | |

| TGG | ACA | TTC | GTC | ACG | GCT | GAT | GAC | TCC | AAA | AAT | GGA | CTG | GAG | AAT | CAT | 96 |
|---|---|---|---|---|---|---|---|---|---|---|---|---|---|---|---|---|
| Trp | Thr | Phe | Val | Thr | Ala | Asp | Asp | Ser | Lys | Asn | Gly | Leu | Glu | Asn | His | |
| -35 | | | | | -30 | | | | | -25 | | | | | -20 | |

| TTT | TGG | AAG | GCA | CGT | GAC | GAA | ATG | AAG | AAC | CGC | GAA | GCC | TCT | AAA | TTG | 144 |
|---|---|---|---|---|---|---|---|---|---|---|---|---|---|---|---|---|
| Phe | Trp | Lys | Ala | Arg | Asp | Glu | Met | Lys | Asn | Arg | Glu | Ala | Ser | Lys | Leu | |
| | | | | -15 | | | | | -10 | | | | | -5 | | |

| GAC | AAA | AAG | GAA | GCC | TGC | TAT | GCG | CCT | GGT | ACT | TTT | TGT | GGC | ATA | AAG | 192 |
|---|---|---|---|---|---|---|---|---|---|---|---|---|---|---|---|---|
| Asp | Lys | Lys | Glu | Ala | Cys | Tyr | Ala | Pro | Gly | Thr | Phe | Cys | Gly | Ile | Lys | |
| | | | 1 | | | | 5 | | | | | | 10 | | | |

| CCC | GGG | CTA | TGC | TGC | AGT | GAG | TTT | TGT | CTC | CCG | GGC | GTC | TGC | TTC | GGT | 240 |
|---|---|---|---|---|---|---|---|---|---|---|---|---|---|---|---|---|
| Pro | Gly | Leu | Cys | Cys | Ser | Glu | Phe | Cys | Leu | Pro | Gly | Val | Cys | Phe | Gly | |
| | 15 | | | | | 20 | | | | | 25 | | | | | |

| GGT | | | | | | | | | | | | | | | | 243 |
|---|---|---|---|---|---|---|---|---|---|---|---|---|---|---|---|---|
| Gly | | | | | | | | | | | | | | | | |
| 30 | | | | | | | | | | | | | | | | |

( 2 ) INFORMATION FOR SEQ ID NO:10:

( i ) SEQUENCE CHARACTERISTICS:
    ( A ) LENGTH: 81 amino acids
    ( B ) TYPE: amino acid
    ( D ) TOPOLOGY: linear ( i i ) MOLECULE TYPE: protein ( x i ) SEQUENCE DESCRIPTION: SEQ ID NO:10:

| Met | Lys | Leu | Thr | Cys | Val | Met | Ile | Val | Ala | Val | Leu | Phe | Leu | Thr | Ala |
|---|---|---|---|---|---|---|---|---|---|---|---|---|---|---|---|
| -51 | -50 | | | | | -45 | | | | | -40 | | | | |

| Trp | Thr | Phe | Val | Thr | Ala | Asp | Asp | Ser | Lys | Asn | Gly | Leu | Glu | Asn | His |
|---|---|---|---|---|---|---|---|---|---|---|---|---|---|---|---|
| -35 | | | | | -30 | | | | | -25 | | | | | -20 |

| Phe | Trp | Lys | Ala | Arg | Asp | Glu | Met | Lys | Asn | Arg | Glu | Ala | Ser | Lys | Leu |
|---|---|---|---|---|---|---|---|---|---|---|---|---|---|---|---|
| | | | | -15 | | | | | -10 | | | | | -5 | |

| Asp | Lys | Lys | Glu | Ala | Cys | Tyr | Ala | Pro | Gly | Thr | Phe | Cys | Gly | Ile | Lys |
|---|---|---|---|---|---|---|---|---|---|---|---|---|---|---|---|
| | | | 1 | | | | 5 | | | | | | 10 | | |

| Pro | Gly | Leu | Cys | Cys | Ser | Glu | Phe | Cys | Leu | Pro | Gly | Val | Cys | Phe | Gly |
|---|---|---|---|---|---|---|---|---|---|---|---|---|---|---|---|
| | 15 | | | | | 20 | | | | | 25 | | | | |

| Gly |
|---|
| 30 |

( 2 ) INFORMATION FOR SEQ ID NO:11:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO (iv) ANTI-SENSE: NO (v) FRAGMENT TYPE: C-terminal (vi) ORIGINAL SOURCE:
(A) ORGANISM: Conus purpurascens (xi) SEQUENCE DESCRIPTION: SEQ ID NO:11:

Cys Phe Gly Gly
1

(2) INFORMATION FOR SEQ ID NO:12:

(i) SEQUENCE CHARACTERISTICS:
(A) LENGTH: 73 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:12:

Met Lys Leu Thr Cys Val Val Ile Val Ala Val Leu Leu Leu Thr Ala
1               5                   10                  15

Cys Gln Leu Ile Thr Ala Asp Asp Ser Arg Gly Thr Gln Lys His Arg
                20                  25                  30

Ala Leu Gly Ser Thr Thr Glu Leu Ser Leu Ser Thr Arg Cys Lys Ser
            35                  40                  45

Pro Gly Ser Ser Cys Ser Pro Thr Ser Tyr Asn Cys Cys Arg Ser Cys
        50                  55                  60

Asn Pro Tyr Thr Lys Arg Cys Tyr Gly
65                  70

(2) INFORMATION FOR SEQ ID NO:13:

(i) SEQUENCE CHARACTERISTICS:
(A) LENGTH: 78 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:13:

Met Lys Leu Thr Cys Met Met Ile Val Ala Val Leu Phe Leu Thr Ala
1               5                   10                  15

Trp Thr Phe Ala Thr Ala Asp Asp Pro Arg Asn Gly Leu Gly Asn Leu
                20                  25                  30

Phe Ser Asn Ala His His Glu Met Lys Asn Pro Glu Ala Ser Lys Leu
            35                  40                  45

Asn Lys Arg Trp Cys Lys Gln Ser Gly Glu Met Cys Asn Leu Leu Asp
        50                  55                  60

Gln Asn Cys Cys Asp Gly Tyr Cys Ile Val Leu Val Cys Thr
65                  70                  75